(12) United States Patent
McLeod et al.

(10) Patent No.: US 8,377,135 B1
(45) Date of Patent: Feb. 19, 2013

(54) TEXTILE-BASED SURGICAL IMPLANT AND RELATED METHODS

(75) Inventors: Alan McLeod, Somerset (GB); Christopher Reah, Taunton (GB); Peter Butcher, Nottingham (GB)

(73) Assignee: NuVasive, Inc., San Diego, CA (US)

( * ) Notice: Subject to any disclaimer, the term of this patent is extended or adjusted under 35 U.S.C. 154(b) by 792 days.

(21) Appl. No.: 12/416,048

(22) Filed: Mar. 31, 2009

Related U.S. Application Data

(60) Provisional application No. 61/041,179, filed on Mar. 31, 2008.

(51) Int. Cl.
*A61F 2/44* (2006.01)

(52) U.S. Cl. ............... 623/17.16; 623/17.15; 623/17.11

(58) Field of Classification Search ..... 623/17.11–17.16
See application file for complete search history.

(56) References Cited

U.S. PATENT DOCUMENTS

| | | | |
|---|---|---|---|
| 3,867,728 A | 2/1975 | Stubstad et al. |
| 3,875,595 A | 4/1975 | Froning |
| 4,280,954 A | 7/1981 | Yannas et al. |
| 4,309,777 A | 1/1982 | Patil |
| 4,349,921 A | 9/1982 | Kuntz |
| 4,458,678 A | 7/1984 | Yannas et al. |
| 4,512,038 A | 4/1985 | Alexander et al. |
| 4,714,469 A | 12/1987 | Kenna |
| 4,759,766 A | 7/1988 | Buettner-Janz et al. |
| 4,759,769 A | 7/1988 | Hedman et al. |
| 4,772,287 A | 9/1988 | Ray et al. |
| 4,863,476 A | 9/1989 | Shepperd |
| 4,863,477 A | 9/1989 | Monson |
| 4,880,429 A | 11/1989 | Stone |
| 4,904,260 A | 2/1990 | Ray et al. |
| 4,911,718 A | 3/1990 | Lee et al. |
| 4,917,704 A | 4/1990 | Frey et al. |
| 4,932,969 A | 6/1990 | Frey et al. |
| 4,932,975 A | 6/1990 | Main et al. |
| 4,946,378 A | 8/1990 | Hirayama et al. |
| 4,955,908 A | 9/1990 | Frey et al. |
| 5,002,576 A | 3/1991 | Fuhrmann et al. |
| 5,007,934 A | 4/1991 | Stone |
| 5,047,055 A | 9/1991 | Bao et al. |
| 5,108,438 A | 4/1992 | Stone |
| 5,123,926 A | 6/1992 | Pisharodi |
| 5,171,280 A | 12/1992 | Baumgartner |
| 5,171,281 A | 12/1992 | Parsons et al. |
| 5,192,326 A | 3/1993 | Bao et al. |
| 5,246,458 A | 9/1993 | Graham |
| 5,258,043 A | 11/1993 | Stone |
| 5,306,308 A | 4/1994 | Gross et al. |

(Continued)

FOREIGN PATENT DOCUMENTS

| | | |
|---|---|---|
| DE | 4315757 C | 11/1994 |
| EP | 0346129 A1 | 12/1989 |

(Continued)

*Primary Examiner* — Thomas J Sweet
*Assistant Examiner* — Seema Mathew
(74) *Attorney, Agent, or Firm* — NuVasive, Inc.; Jonathan Spangler; Heather Prado

(57) ABSTRACT

A combination pre-filled and in situ filled implant for the replacement of an intervertebral disc of the spine, including a textile core and a flange with apertures dimensioned to receive screws or other affixation elements. The combination pre-filled and in situ filled implant may also have attached side pockets comprised of extra layers of embroidered fabric. The pockets on the implant may serve a dual purpose: to facilitate insertion and to expand the dimensions of the implant after insertion.

12 Claims, 27 Drawing Sheets

U.S. PATENT DOCUMENTS

| | | | |
|---|---|---|---|
| 5,306,309 A | 4/1994 | Wagner et al. | |
| 5,383,884 A | 1/1995 | Summers | |
| 5,401,269 A | 3/1995 | Buttner-Janz et al. | |
| 5,458,643 A | 10/1995 | Oka et al. | |
| 5,507,816 A | 4/1996 | Bullivant | |
| 5,522,898 A | 6/1996 | Bao | |
| 5,534,023 A | 7/1996 | Henley | |
| 5,534,028 A | 7/1996 | Bao et al. | |
| 5,534,030 A | 7/1996 | Navarro et al. | |
| 5,540,688 A | 7/1996 | Navas | |
| 5,545,229 A | 8/1996 | Parsons et al. | |
| 5,549,679 A | 8/1996 | Kuslich | |
| 5,562,736 A | 10/1996 | Ray et al. | |
| 5,562,738 A | 10/1996 | Boyd et al. | |
| 5,571,189 A | 11/1996 | Kuslich | |
| 5,645,597 A | 7/1997 | Krapiva | |
| 5,674,296 A | 10/1997 | Bryan et al. | |
| 5,676,702 A | 10/1997 | Ratron | |
| 5,683,464 A | 11/1997 | Wagner et al. | |
| 5,683,465 A | 11/1997 | Shinn et al. | |
| 5,702,450 A | 12/1997 | Bisserie | |
| 5,702,454 A | 12/1997 | Baumgartner | |
| 5,705,780 A | 1/1998 | Bao | |
| 5,716,416 A | 2/1998 | Lin | |
| 5,749,916 A | 5/1998 | Richelsoph | |
| 5,755,796 A | 5/1998 | Ibo et al. | |
| 5,976,186 A | 11/1999 | Bao et al. | |
| 5,990,378 A | 11/1999 | Ellis | |
| 6,093,205 A | 7/2000 | McLeod et al. | |
| 6,110,210 A | 8/2000 | Norton et al. | |
| 6,174,330 B1 | 1/2001 | Stinson | |
| 6,187,043 B1 | 2/2001 | Ledergerber | |
| 6,270,530 B1 | 8/2001 | Eldridge et al. | |
| 6,283,998 B1 | 9/2001 | Eaton | |
| 6,371,990 B1 | 4/2002 | Ferree | |
| 6,416,776 B1 | 7/2002 | Shamie | |
| 6,419,704 B1 | 7/2002 | Ferree | |
| 6,428,544 B1 | 8/2002 | Ralph et al. | |
| 6,447,548 B1 | 9/2002 | Ralph et al. | |
| 6,620,196 B1 | 9/2003 | Trieu | |
| 6,712,853 B2 * | 3/2004 | Kuslich | 623/17.16 |
| 6,746,485 B1 | 6/2004 | Zucherman et al. | |
| 6,827,743 B2 | 12/2004 | Eisermann et al. | |
| 6,893,466 B2 | 5/2005 | Trieu | |
| 6,955,689 B2 | 10/2005 | Ryan et al. | |
| 7,004,970 B2 | 2/2006 | Cauthen, III et al. | |
| 7,018,412 B2 | 3/2006 | Ferreira et al. | |
| 7,066,960 B1 | 6/2006 | Dickman | |
| 7,153,325 B2 | 12/2006 | Kim et al. | |
| 7,214,225 B2 | 5/2007 | Ellis et al. | |
| 7,318,840 B2 | 1/2008 | McKay | |
| 7,338,531 B2 | 3/2008 | Ellis et al. | |
| 7,341,601 B2 | 3/2008 | Eisermann et al. | |
| 7,445,634 B2 | 11/2008 | Trieu | |
| 7,588,574 B2 | 9/2009 | Assell et al. | |
| 7,604,653 B2 | 10/2009 | Kitchen | |
| 7,618,457 B2 | 11/2009 | Hudgins | |
| 7,682,400 B2 | 3/2010 | Zwirkoski | |
| 7,758,647 B2 | 7/2010 | Arnin et al. | |
| 7,887,593 B2 | 2/2011 | McKay et al. | |
| 7,905,922 B2 | 3/2011 | Bergeron | |
| 7,959,683 B2 | 6/2011 | Semler et al. | |
| 2002/0026244 A1 | 2/2002 | Trieu | |
| 2002/0058947 A1 | 5/2002 | Hochschuler et al. | |
| 2002/0077701 A1 | 6/2002 | Kuslich | |
| 2002/0077702 A1 | 6/2002 | Castro | |
| 2002/0123750 A1 | 9/2002 | Eisermann et al. | |
| 2003/0129257 A1 | 7/2003 | Nies et al. | |
| 2003/0220691 A1 | 11/2003 | Songer et al. | |
| 2004/0113801 A1 | 6/2004 | Gustafson et al. | |
| 2004/0243237 A1 | 12/2004 | Unwin et al. | |
| 2005/0015140 A1 | 1/2005 | deBeer | |
| 2005/0027364 A1 | 2/2005 | Kim et al. | |
| 2005/0055094 A1 | 3/2005 | Kuslich | |
| 2005/0119725 A1 | 6/2005 | Wang et al. | |
| 2005/0177240 A1 | 8/2005 | Blain | |
| 2005/0192669 A1 | 9/2005 | Zdeblick et al. | |
| 2005/0197702 A1 * | 9/2005 | Coppes et al. | 623/17.12 |
| 2005/0228500 A1 | 10/2005 | Kim et al. | |
| 2005/0267580 A1 * | 12/2005 | Suddaby | 623/17.12 |
| 2006/0085080 A1 | 4/2006 | Bechgaard et al. | |
| 2006/0089721 A1 * | 4/2006 | Muhanna et al. | 623/17.16 |
| 2006/0116774 A1 | 6/2006 | Jones et al. | |
| 2006/0200137 A1 | 9/2006 | Soboleski et al. | |
| 2006/0293662 A1 | 12/2006 | Boyer, II et al. | |
| 2007/0055373 A1 | 3/2007 | Hudgins et al. | |
| 2007/0100453 A1 | 5/2007 | Parsons et al. | |
| 2007/0112428 A1 | 5/2007 | Lancial | |
| 2007/0135922 A1 * | 6/2007 | Trieu | 623/17.12 |
| 2007/0173943 A1 * | 7/2007 | Dulak et al. | 623/17.16 |
| 2007/0233259 A1 * | 10/2007 | Muhanna et al. | 623/17.12 |
| 2008/0027554 A1 * | 1/2008 | Talmadge | 623/17.16 |
| 2008/0154375 A1 * | 6/2008 | Serhan et al. | 623/17.16 |
| 2008/0154382 A1 * | 6/2008 | de Villiers et al. | 623/17.16 |
| 2008/0161929 A1 * | 7/2008 | McCormack et al. | 623/17.16 |
| 2008/0228273 A1 | 9/2008 | McLeod et al. | |
| 2008/0269900 A1 | 10/2008 | Reah et al. | |
| 2008/0288073 A1 * | 11/2008 | Renganath et al. | 623/17.12 |
| 2008/0306593 A1 | 12/2008 | McLeod et al. | |
| 2008/0306595 A1 | 12/2008 | McLeod et al. | |
| 2009/0105826 A1 | 4/2009 | McLeod et al. | |
| 2009/0171461 A1 * | 7/2009 | Conner et al. | 623/17.11 |
| 2010/0286778 A1 | 11/2010 | Eisermann et al. | |
| 2010/0320639 A1 | 12/2010 | Reah et al. | |
| 2011/0060366 A1 | 3/2011 | Heim et al. | |

FOREIGN PATENT DOCUMENTS

| | | |
|---|---|---|
| EP | 0346269 A2 | 12/1989 |
| EP | 0453393 A1 | 10/1991 |
| EP | 0179695 B1 | 12/1991 |
| EP | 0599419 A2 | 6/1994 |
| EP | 0621020 A1 | 10/1994 |
| EP | 0662309 A1 | 7/1995 |
| EP | 0563332 B1 | 8/1995 |
| EP | 0747025 A1 | 12/1996 |
| EP | 0820740 A1 | 1/1998 |
| EP | 0744162 B1 | 2/2003 |
| EP | 1318167 A2 | 6/2003 |
| WO | WO 91/00713 A1 | 1/1991 |
| WO | WO 92/10982 A1 | 7/1992 |
| WO | WO 93/16664 A1 | 9/1993 |
| WO | WO 95/19153 A1 | 7/1995 |
| WO | WO 95/25487 A1 | 9/1995 |
| WO | WO 95/31946 A1 | 11/1995 |
| WO | WO 96/11639 A1 | 4/1996 |
| WO | WO 96/11642 A1 | 4/1996 |
| WO | WO 96/40014 A1 | 12/1996 |
| WO | WO 97/20526 A1 | 6/1997 |
| WO | WO 98/22050 A1 | 5/1998 |
| WO | WO 01/21246 A1 | 3/2001 |
| WO | WO 02/11650 A2 | 2/2002 |
| WO | WO 03/068111 A1 | 8/2003 |
| WO | WO 03/077806 A1 | 9/2003 |
| WO | WO 2004/002374 A1 | 1/2004 |
| WO | WO 2005/004941 A1 | 1/2005 |
| WO | WO 2005/092211 A1 | 10/2005 |
| WO | WO 2005/092247 A1 | 10/2005 |
| WO | WO 2005/092248 A1 | 10/2005 |
| WO | WO 2005/112833 A1 | 12/2005 |
| WO | WO 2006/133130 A2 | 12/2006 |
| WO | WO 2007/012070 A2 | 1/2007 |
| WO | WO 2007/020449 A2 | 2/2007 |
| WO | WO 2007/067547 A2 | 6/2007 |
| WO | WO 2008/098125 A2 | 8/2008 |
| WO | WO 2008/131310 A1 | 10/2008 |
| WO | WO 2009/006455 A1 | 1/2009 |

* cited by examiner

TEXTILE-BASED SURGICAL IMPLANT AND RELATED METHODS

CROSS-REFERENCES TO RELATED APPLICATIONS

The present application is a nonprovisional patent application claiming the benefit of priority under 35 U.S.C. §119(e) from U.S. Provisional Patent Application Ser. No. 61/041,179, filed on Mar. 31, 2008, the entire contents of which is hereby expressly incorporated by reference into this disclosure as if set forth fully herein. The present application also incorporates by reference the following documents into this disclosure in their entireties: U.S. Pat. No. 6,093,205 issued Jul. 25, 2000 and entitled "Surgical Implant;" International Patent Application No. PCT/US2008/060944, filed Apr. 18, 2008 and entitled "Textile-Based Surgical Implants and Related Methods;" and International Patent Application No. PCT/US2008/068868, filed Jun. 30, 2008 and entitled "Facet Joint Implant and Related Methods."

BACKGROUND OF THE INVENTION

I. Field of the Invention

The present invention relates generally to surgical implants and, more particularly, to textile-based implants for surgical implantation and related methods of manufacture and use.

II. Discussion of the Prior Art

Surgical implants exist for myriad clinical needs, including (by way of example only) spine surgery to treat diseased or damaged intervertebral discs. Increasingly this treatment involves replacing all or part of the disc with a prosthesis. Disc prostheses based on either articulating metal plates or metal end plates supporting a polyethylene spacer are now in clinical use. These mechanical total disc replacements help to reduce the loss in spinal mobility and the degeneration of adjacent discs commonly associated with fusion.

While mechanical total disc replacements are a great improvement over fusion, some surgeons would rather use non-mechanical motion preserving implants. Previously there has been developed a textile-based total disc replacement having a textile-based core provided in a textile retaining jacket. Such an implant is described in commonly owned and co-pending International Patent Application PCT/US2008/060944, filed Apr. 18, 2008 and entitled "Textile-Based Surgical Implants and Related Methods," the entire contents of which are incorporated into this disclosure. The textile-based implant is advantageous in that it allows tissue ingrowth and is generally compliant and therefore is capable of restoring disc height and preserving the motion of the spinal unit. While such textile-based motion preserving spinal implants show great promise, there is still room for improvement.

The present invention is directed to improving textile-based implants, including but not limited to textile-based motion preserving spinal implants.

SUMMARY OF THE INVENTION

The present invention accomplishes this goal by providing a combination pre-filled and in situ filled implant. According to one broad aspect of the present invention, the implant may include a textile core and a flange with apertures dimensioned to receive screws or other affixation elements. The combination pre-filled and in situ filled implant may also have attached side pockets comprised of extra layers of embroidered fabric. The pockets on the implant may serve a dual purpose: to facilitate insertion and to expand the dimensions of the implant after insertion.

A variety of materials can be used to form the spacer and/or encapsulating jacket of the implant. The spacer is preferably formed of biocompatible material. In one preferred embodiment, the spacer is formed of a textile/fabric material throughout. The spacer may be constructed from any of a variety of fibrous materials, for example including but not limited to polyester fiber, polypropylene, polyethylene, ultra high molecular weight polyethylene (UHMWPe), poly-ether-ether-ketone (PEEK), carbon fiber, glass, glass fiber, polyaramide, metal, copolymers, polyglycolic acid, polylactic acid, biodegradable fibers, silk, cellulosic and polycaprolactone fibers. The spacer may be manufactured via any number of textile processing techniques (e.g. embroidery, weaving, three-dimensional weaving, knitting, three-dimensional knitting, injection molding, compression molding, cutting woven or knitted fabrics, etc.). In another preferred embodiment, the spacer is comprised of an elastomeric component (e.g. silicon) encapsulated in fabric. Furthermore, the spacer may be provided in any number of suitable dimensions depending upon the surgical application and patient pathology.

The jacket may be constructed from any of a variety of fibrous materials, for example including but not limited to polyester fiber, polypropylene, polyethylene, ultra high molecular weight polyethylene (UHMWPe), poly-ether-ether-ketone (PEEK), carbon fiber, glass, glass fiber, polyaramide, metal, copolymers, polyglycolic acid, polylactic acid, biodegradable fibers, silk, cellulosic and polycaprolactone fibers. The jacket may be manufactured via any number of textile processing techniques (e.g. embroidery, weaving, three-dimensional weaving, knitting, three-dimensional knitting, injection molding, compression molding, cutting woven or knitted fabrics, etc.). The jacket may encapsulate the spacer fully (i.e. disposed about all surfaces of the spacer) or partially (i.e. with one or more apertures formed in the jacket allowing direct access to the spacer). The various layers and/or components of the spacer may be attached or unattached to the encapsulating jacket. The jacket may optionally include one or more fixation elements for retaining the jacket in position after implantation, including but to limited to one or more flanges extending from or otherwise coupled to the jacket and screws or other affixation elements (e.g. nails, staples sutures, tacks, adhesives, etc.) to secure the flange to an adjacent anatomical structure (e.g. vertebral body). This may be facilitated by providing one or more apertures within the flange dimensioned to receive the screws or other fixation elements.

The materials selected to form the spacer and/or jacket may be specifically selected depending upon the target location/use within the body (e.g. spinal, general orthopedic, and/or general surgical). For example in many instances it may be preferable to select UHMWPe fibers in order to generate a specific tissue response, such as limited tissue and/or bony ingrowth. In some instances it may be desirable to modify the specific fibers used, such as providing a surface modification to change or enhance a desired tissue response.

After the implant has been inserted into the intervertebral disc space, the pockets may be filled in situ. The pockets of the implant may be filled with any biocompatible material including but not limited to textile material (e.g. polyester), filler pads (e.g. embroidered polyester, elastomeric and/or viscoelastic filing elements), and/or fibrous material (e.g. polyester fiber, elastomeric fibers, etc.). In all instances, filling the pockets of the implant in situ provides for the expansion of the physical dimensions of the implant.

The combination pre-filled and in situ filled implant advantageously allows for minimally invasive surgical procedures. The pre-filled implant with pockets may be inserted through a relatively small operative corridor. Subsequently, once the implant is in situ, the pockets may be filled, thereby increasing the size of the implant. The overall benefit is an enlarged implant which may be introduced through a minimally invasive procedure, as opposed to opening an expansive operative corridor in order to accommodate a larger pre-filled implant. By filling the pockets of the implant in situ, the final dimensions of the implant may be significantly larger than as originally placed. As a result, the larger footprint of the combination pre-filled and in situ filled implant provides additional support within the intervertebral disc space and throughout the spine. The larger footprint of the implant also provides for more tissue ingrowth due to the increased surface contact between the vertebrae and the implant, which may help to anchor the implant in position.

The combination pre-filled and in situ filled implant may be inserted through any number of suitable surgical approaches, including but not limited to lateral, anterior, anterior-lateral, postero-lateral, and/or posterior approaches. It is envisioned that the pocket feature of the implant may be integrated into any type of surgical implant. In all cases, the implant having been deposited within a joint and filled in situ, provides extensive support and restores the physiologic movements of the joint.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The combination pre-filled and in situ filled implant disclosed herein boasts a variety of inventive features and components that warrant patent protection, both individually and in combination.

Figure 1:
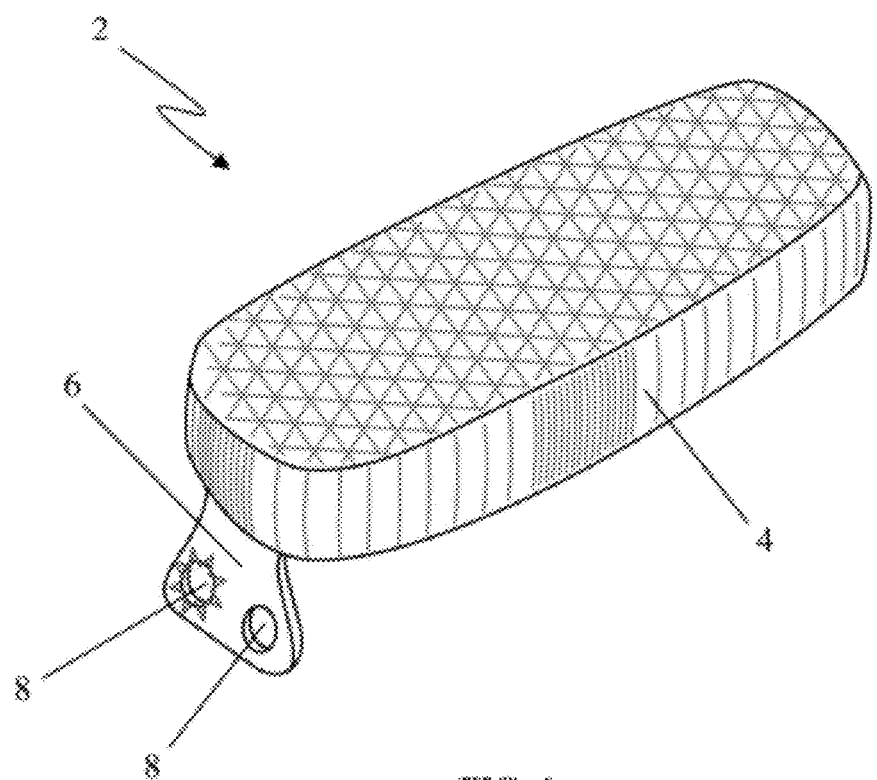
FIG. 1 is a perspective view of a laterally-inserted textile-based implant according to one embodiment of the present invention.
Figure 2:
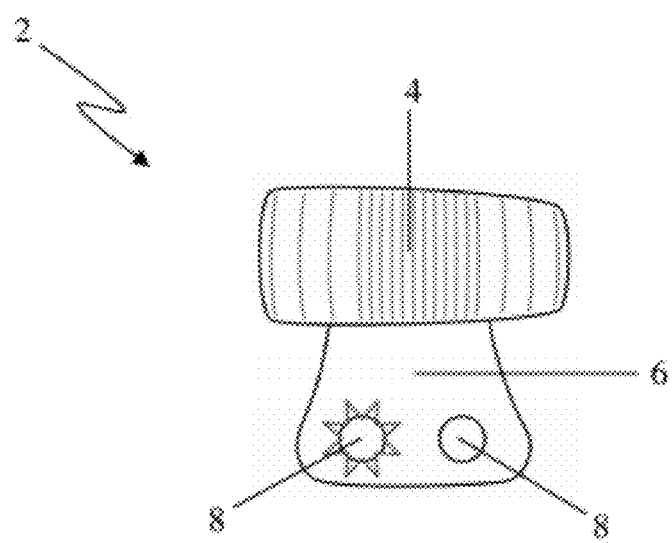
FIG. 2 is an end view of the textile-based implant of FIG. 1.

FIGS. 1 & 2 illustrate an example of a pre-filled textile-based implant 2, according to one embodiment of the present invention. The implant 2 may be inserted through any number of suitable surgical approaches, including but not limited to lateral, anterior, anterior-lateral, postero-lateral, and/or posterior approaches. When applied to spine surgery and inserted into an intervertebral disc space (not shown), the implant 2 restores the normal height of the intervertebral disc space, while advantageously preserving the natural (or approximately natural) motion of the spine. The implant 2 may be comprised of a textile core 4 and a flange 6 with apertures 8 dimensioned to receive screws or other affixation elements.

By way of example only, the implant 2 is specifically dimensioned for lateral insertion (i.e. insertion from the side of a patient) of the implant 2 using a minimally invasive surgical technique. Although shown as having a generally rectangular shape, the implant 2 may be provided in any number of suitable dimensions depending upon the surgical application, patient pathology, and surgical approach of insertion. In all instances, the implant 2 restores the normal height of the intervertebral disc space, while advantageously preserving the natural motion of the spine. In addition, a variety of features may be incorporated into the implant 2 to match the natural (or approximately natural) curvature of the spine, including but not limited to an anatomical dome shape or tapered shape, similar to that shown and described in commonly owned and co-pending International Patent Application PCT/US2008/060944, filed Apr. 18, 2008 and entitled "Textile-Based Surgical Implants and Related Methods," the complete disclosure of which is hereby incorporated by reference in this application as if set forth entirely herein.

Figure 3:
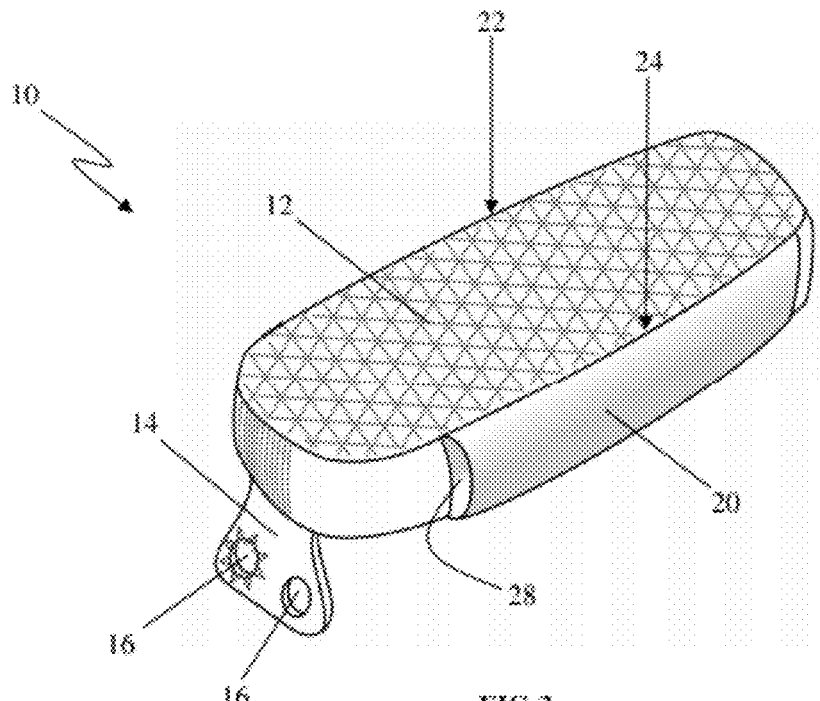
FIG. 3 is a perspective view of a laterally-inserted textile-based implant with pockets according to another embodiment of the present invention.
Figure 4:
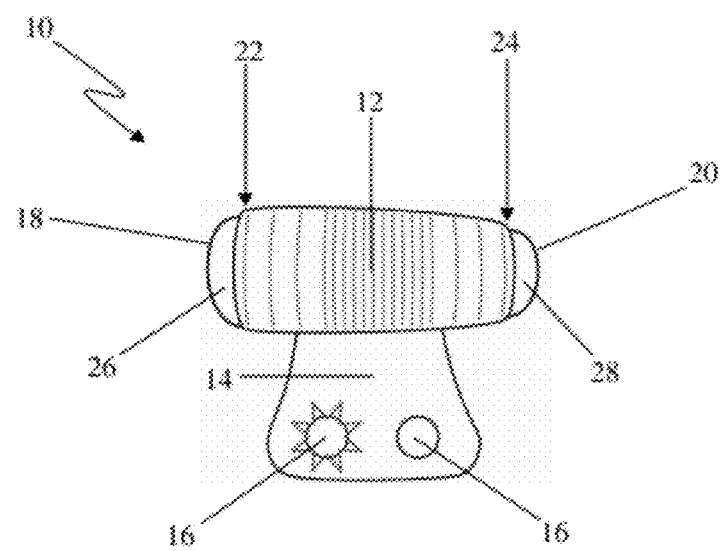
FIG. 4 is an end view of the textile-based implant of FIG. 3.
Figure 5:
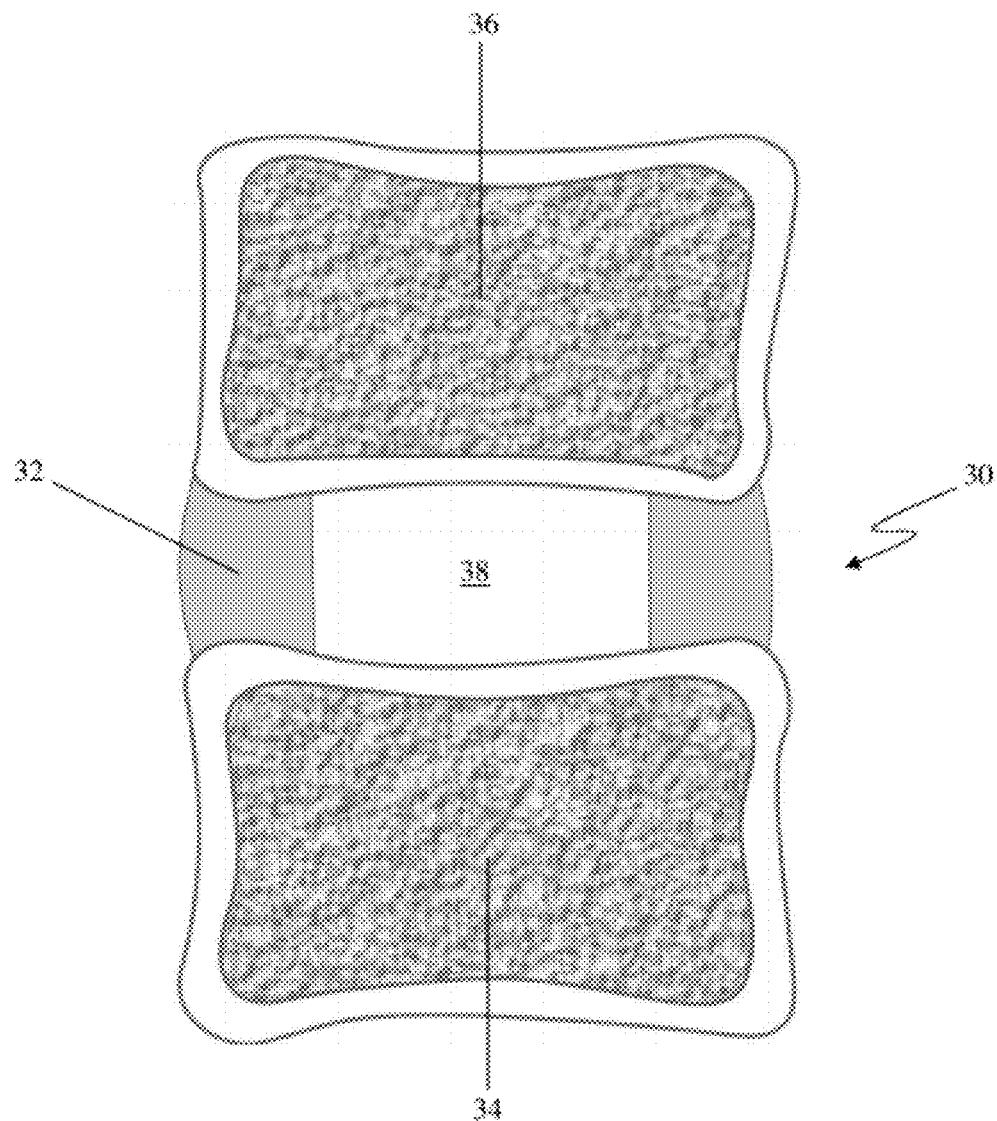
FIG. 5 is a lateral view of an intervertebral disc space after a partial discectomy removing the central portion of the intervertebral disc, according to one aspect of the present invention.
Figure 6:
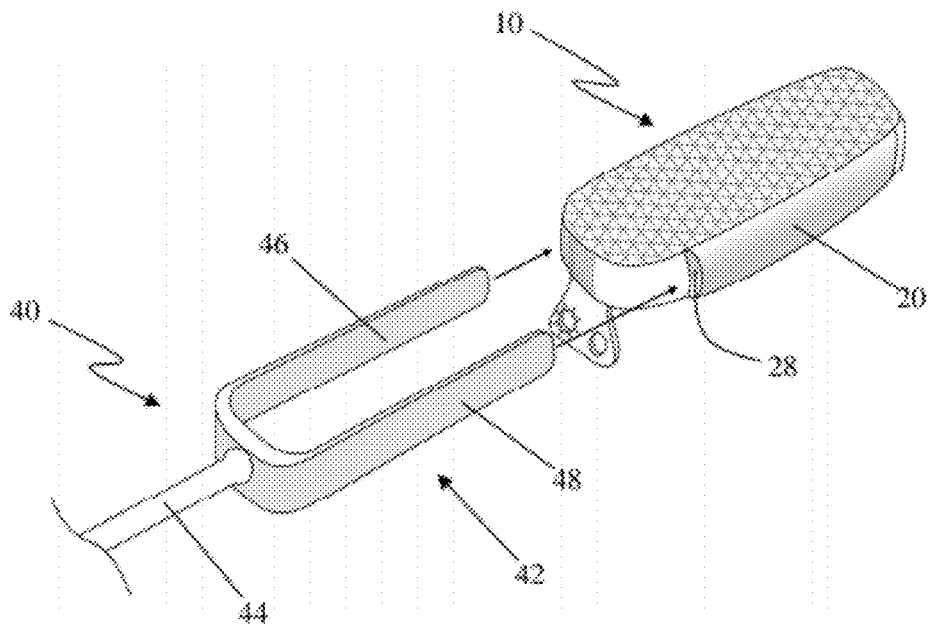
FIG. 6 is a perspective view of the implant of FIG. 3 and an inserter assembly, according to a first embodiment of the present invention for insertion of an implant into an intervertebral disc space.
Figure 7:
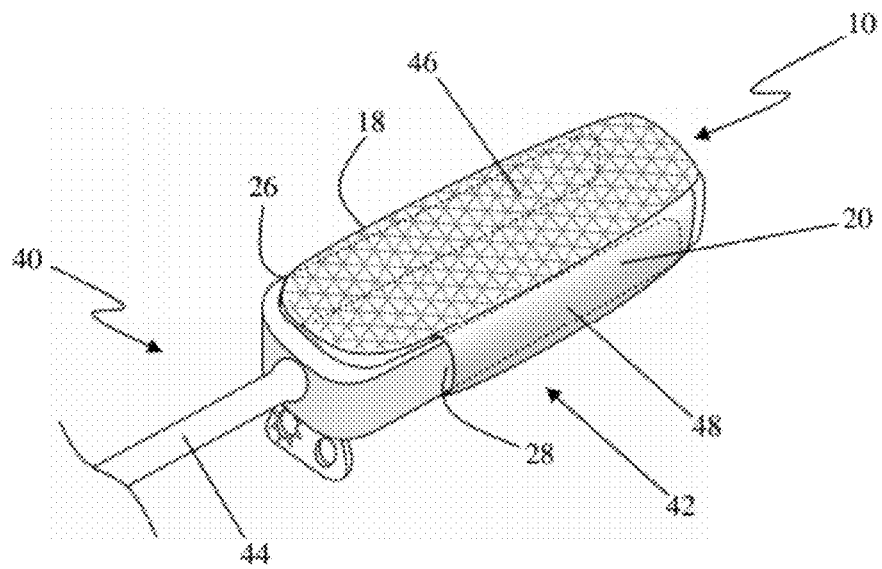
FIG. 7 is a perspective view of the inserter assembly of FIG. 6 engaged with the implant.
Figure 8:
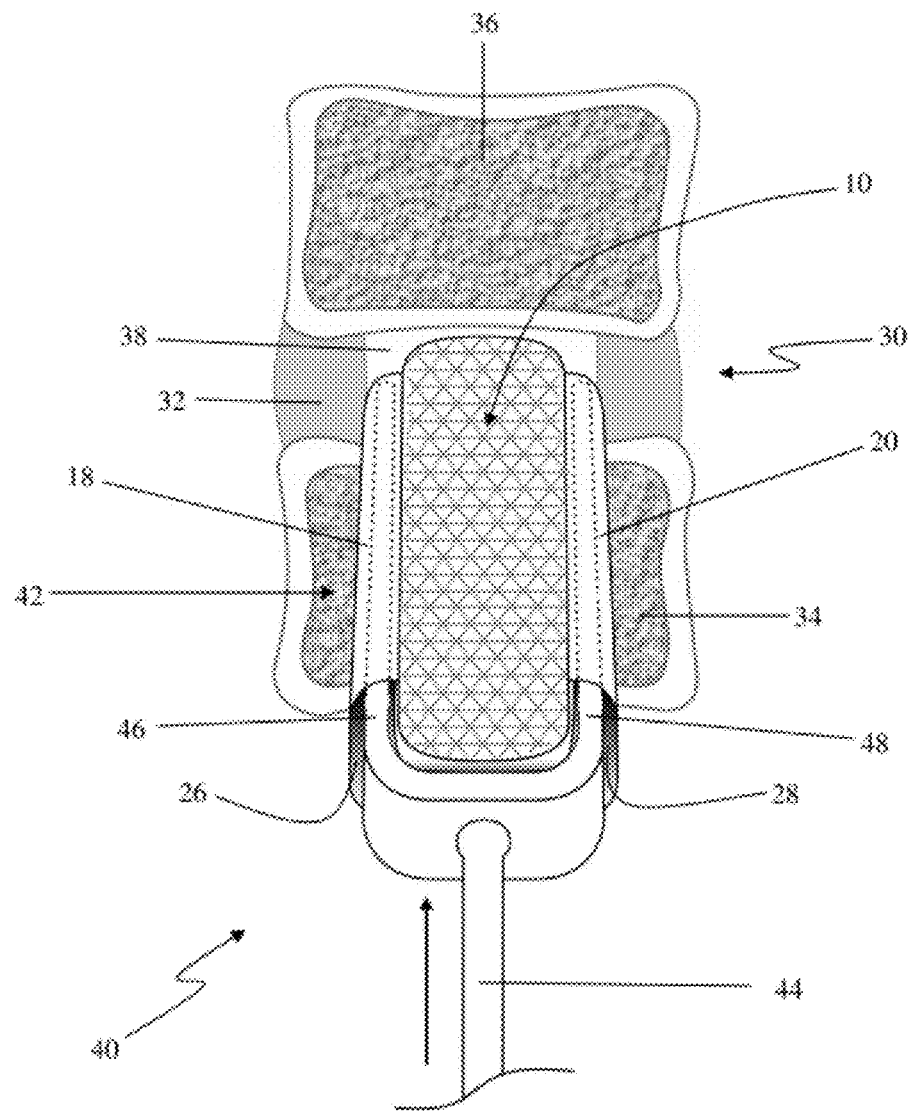
FIG. 8 is a perspective view of the inserter assembly of FIG. 7 inserting the implant into the prepared intervertebral disc space of FIG. 5.
Figure 9:
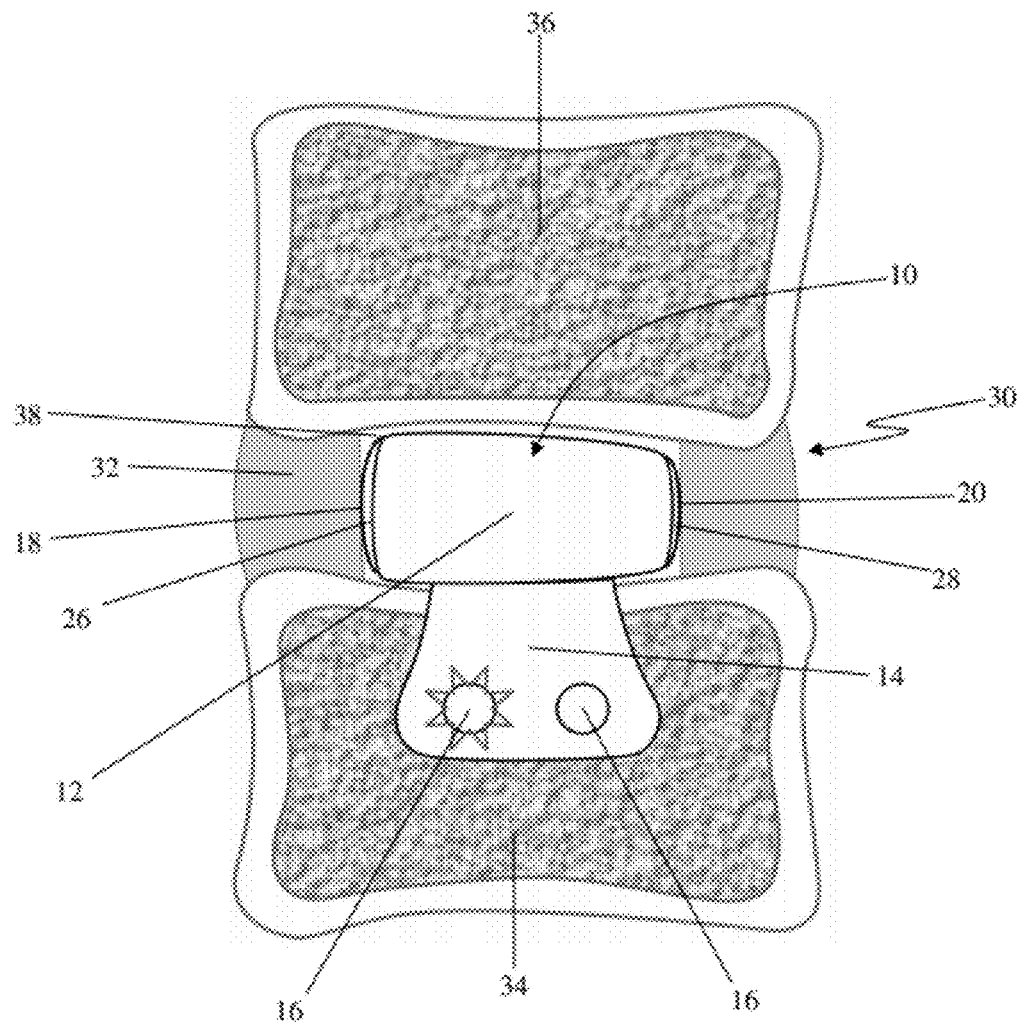
FIG. 9 is a lateral view of the implant of FIG. 8 in situ after insertion.
Figure 10:
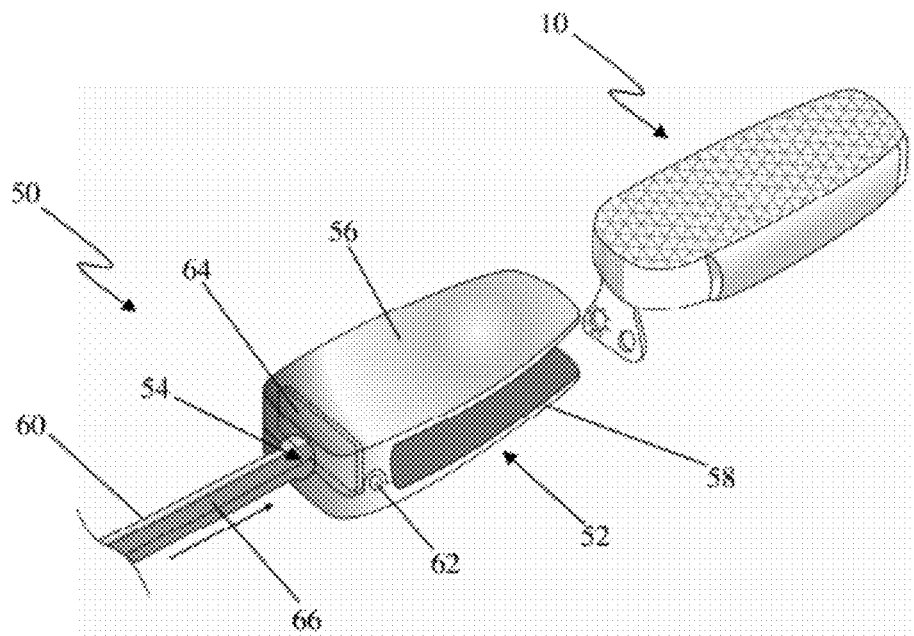
FIG. 10 is a perspective view of the implant of FIG. 3 and an inserter assembly, according to a second embodiment of the present invention for insertion of an implant into an intervertebral disc space.
Figure 11:
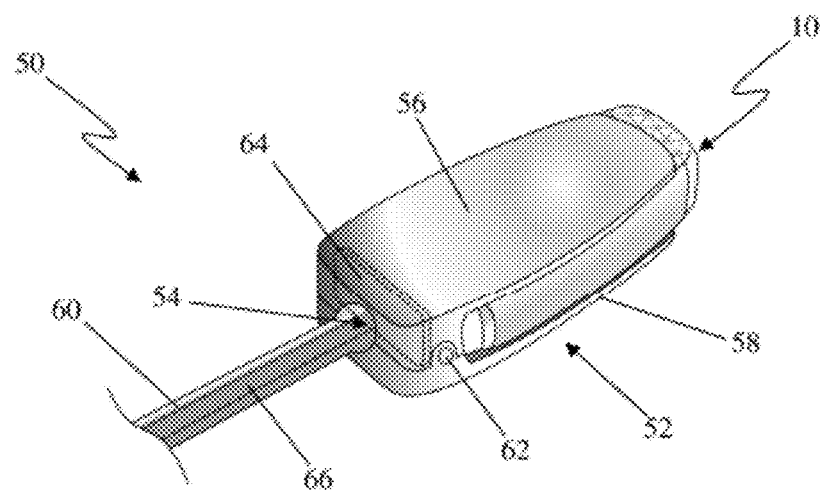
FIG. 11 is a perspective view of the inserter assembly in FIG. 10 engaged with the implant.
Figure 12:
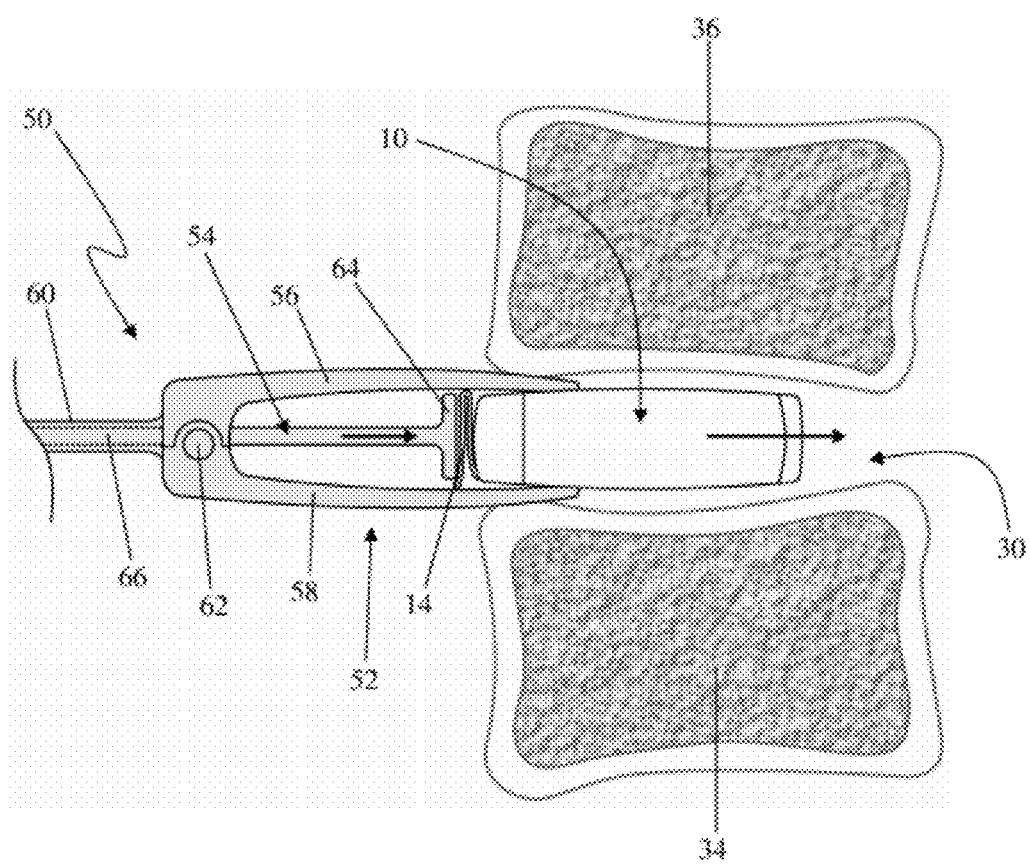
FIG. 12 is a side cross-sectional view of the inserter assembly of FIG. 11 inserting the implant laterally into an intervertebral disc space.
Figure 13:
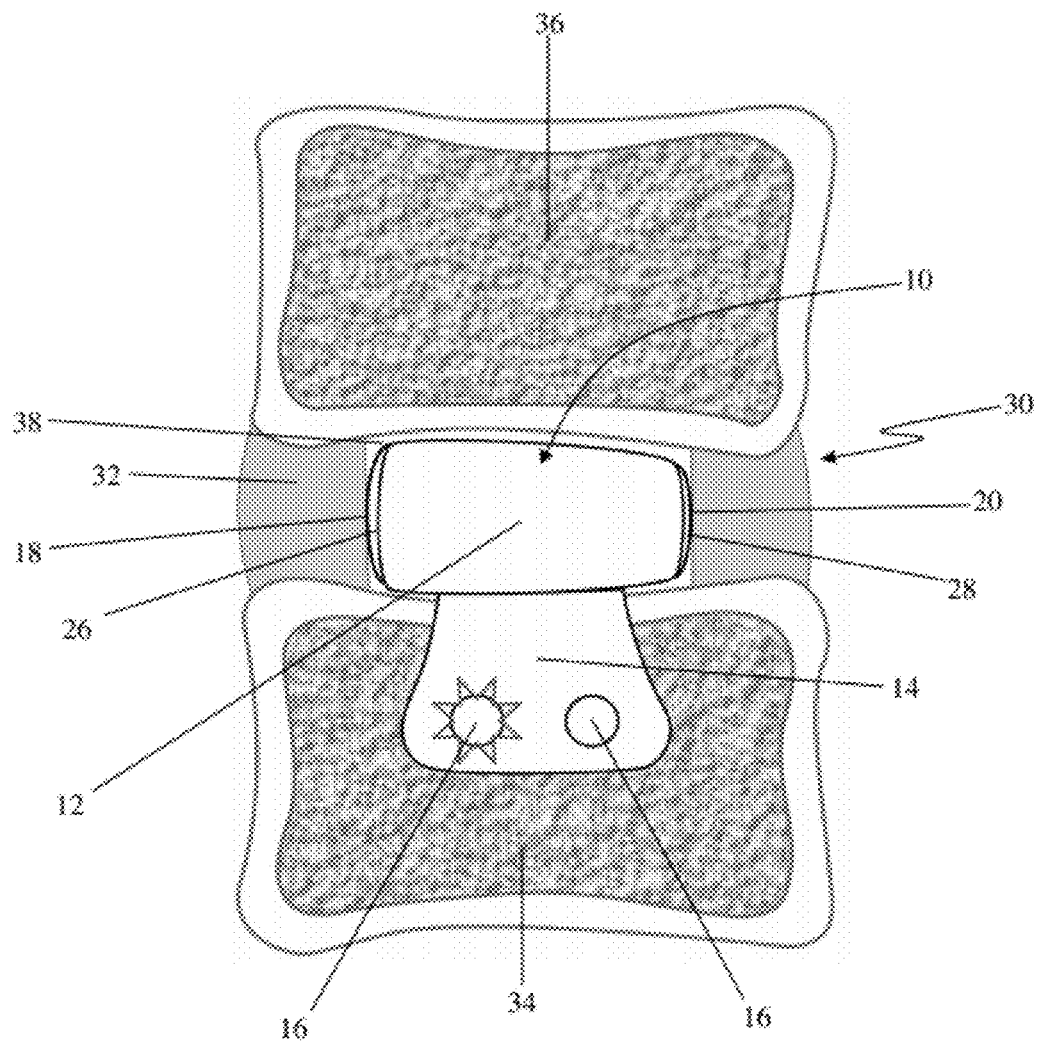
FIG. 13 is a lateral view of the implant of FIG. 12 in situ after insertion.

FIGS. 3 & 4 illustrate an example of a combination pre-filled and in situ filled implant 10, according to a second embodiment of the present invention. Similar to the pre-filled implant 2 described above, the combination pre-filled and in situ filled implant 10 has a textile core 12 and a flange 14 with apertures 16 dimensioned to receive screws or other fixation elements. However, in this embodiment, the implant 10 has a pair of pockets 18, 20 attached to the sides 22, 24, respectively, of the implant 10. By way of example only, the pockets 18, 20 comprise extra layers of embroidered fabric on the sides 22, 24 of the implant 10 and have proximal openings 26, 28, respectively. Pockets 18, 20 on the implant 10 may serve a dual purpose: (1) to facilitate insertion of the implant into an intervertebral disc space, and (2) to expand the dimensions of the implant 10 after insertion. As opposed to filling the entire implant 10 in situ, the pre-filled core 12 of the implant may incorporate various desired features, such as for example a contoured shape, preset structure, taper angle, and/or specified stiffness. While the core 12 of the implant 10 comprises the predetermined pre-filled volume of the implant 10, the pockets 18, 20 of the implant 10 allow for the implant 10 to be filled in situ, thereby increasing the volume/anchoring area of the implant 10 and offering additional support within an intervertebral disc space.

FIGS. 5-9 illustrate an example of a first method for inserting a combination pre-filled and in situ filled implant 10 into an intervertebral disc space 30. The first step in this method involves a partial or total discectomy of the intervertebral disc 32 in order to facilitate the insertion of the implant 10 within the intervertebral disc space 30 between two adjacent vertebrae 34, 36. More specifically, at least a portion of the intervertebral disc 32 is removed in order to create a prepared disc space 38 in which the implant 10 will be inserted. The prepared disc space 38 is preferably dimensioned to receive the implant 10.

The second step in the first method for inserting an implant 10 into an intervertebral disc space 30 involves engaging the inserter assembly 40 with the implant 10. The inserter assembly 40 is designed to releasably maintain the implant 10 in the proper orientation for insertion. The implant 10 is introduced into the intervertebral disc space 30 while engaged with the inserter assembly 40 and thereafter released. Preferably, the inserter assembly 40 includes a distal engagement region 42 and an elongated handling member 44. The inserter assembly 40 may be composed of any material suitable for inserting an implant 10 into an intervertebral disc space 30, including but not limited to metal (e.g. titanium, stainless steel, etc.), ceramic, and/or polymer compositions.

According to this particular embodiment, the distal engagement region 42 is comprised of two insertion prongs 46, 48. The insertion prongs 46, 48 are parallel to each other, and generally vertically oriented such that the prongs are configured to engage the sides 22, 24 of the implant 10. The shape of the insertion prongs 46, 48 is generally planar rectangular, but may take the form of any geometric shape necessary to interact with the implant 10, including but not limited to generally oval, square, and triangular. The handling member 44 is generally cylindrical in shape, but also may be provided in any suitable geometric shape, including (but not limited to) generally oval, square and triangular. The handling member 44 allows a clinician to manipulate the tool during an implant insertion procedure.

The insertion assembly 40 engages with the implant 10 by sliding the insertion prongs 46, 48 into the openings 26, 28 of the pockets 18, 20, respectively, on the implant 10. Although slideable engagement is described, any suitable means of engagement may be used to engage the inserter assembly 40 with the implant 10, including but not limited to a threaded engagement, snapped engagement, hooks, and/or compressive force. Once the insertion prongs 46, 48 are inside the pockets 18, 20 of the implant 10, the inserter assembly 40 releasably maintains the implant 10 in the proper orientation for insertion. The implant 10 may then be introduced into the prepared disc space 38 while engaged with the inserter assembly 40 and thereafter released.

It will be appreciated that the number of insertion prongs 46, 48 and pockets 18, 20 is set forth by way of example only and may be increased or decreased without departing from the scope of the present invention. The arrangement and placement of the pockets 18, 20 is set forth by way of example as well and may be varied without departing from the scope of the present invention. In all instances, the implant 10, having been deposited in the intervertebral disc space 30, facilitates normal spinal functionality over time by maintaining a restored intervertebral disc height as well as retaining motion.

FIGS. 10-13 illustrate an example of an inserter assembly 50 used for inserting the implant 10 into the intervertebral disc space 30 according to a second embodiment of the present invention. According to this embodiment, the inserter assembly 50 includes a clamping mechanism 52, an internal deployment mechanism 54, and an elongated tubular handling member 60. The inserter assembly 50 may be composed of any material suitable for inserting an implant 10 into an intervertebral disc space 30, including but not limited to metal (e.g. titanium, stainless steel, etc.), ceramic, and/or polymer compositions.

The clamping mechanism 52 of the inserter assembly 50 is comprised of an upper clamping plate 56 and a lower clamping plate 58. The upper and lower clamping plates 56, 58, are hinged together through a hinge element 62. In an alternative embodiment, the upper and lower clamping plates 56, 58 are not hinged but rather biased toward one another. The clamping plates 56, 58 are parallel to each other, and generally horizontally oriented that the plates are configured to engage the top and bottom of the implant 10. The shape of the clamping plates 56, 58 is generally planar rectangular, but may take the form of any geometric shape necessary to interact with the implant 10. The clamping mechanism 52 is configured to clamp the implant 10 in between the clamping plates 56, 58. The handling member 60 of the inserter assembly 50 is generally cylindrical in shape and may be configured to house the length of the internal deployment mechanism 54. The elongated handling member 60 allows a clinician to manipulate the clamping mechanism 52 during an implant insertion procedure.

The internal deployment mechanism 54 of the inserter assembly 50 is comprised of a guiding plate 64 and a handle 66. The guiding plate 64 is generally planar rectangular in shape and vertically oriented, but may take any form necessary to deploy the implant 10 from the clamping plates 56, 58 of the inserter assembly 50 into the intervertebral disc space 30. The handle 66 of the deployment mechanism 54 is generally cylindrical in shape and has a smaller circumference than the handling member 60 such that the handle 66 is dimensioned to fit within the handling member 60. The handle 66 of the deployment mechanism 54 allows a clinician to manipulate the deployment mechanism 54 during an implant insertion procedure. The deployment mechanism 54 may be configured to move separately from the clamping mechanism 52, such that the internal deployment mechanism 54 extends away from the handling member 60 of the clamping mechanism 52 in order to deploy the implant 10 into position within the intervertebral disc space 30.

The inserter assembly 50 engages with the implant 10 by clamping the implant 10 in between the clamping plates 56, 58. Although clamping engagement is described herein, any suitable means of engagement may be used to engage the clamping plates 56, 58 of the inserter assembly 50 with the implant 10, including but not limited to a threaded engagement, slideable engagement, snapped engagement, hooks, and/or compressive force. Once the upper clamping plate 56 and the lower clamping plate 58 securely hold the top and bottom, respectively, of the implant 10, the inserter assembly 50 releasably maintains the implant 10 in proper orientation for insertion. The implant 10 may then be simultaneously introduced into an intervertebral disc space 30 while engaged with the inserter assembly 50.

More specifically, once the clamping mechanism 52 of the inserter assembly 50 brings the implant 10 to the intervertebral disc space 30 between two vertebrae 34, 36, the guiding plate 64 of the deployment mechanism 54 pushes the implant 10 into the prepared disc space 38. The guiding plate 64 of the internal deployment mechanism 54 guides and deploys the implant 10 from the inserter assembly 50 into the intervertebral disc space 30. Although described herein as having a deployment mechanism 54, the inserter assembly 50 of the second embodiment may be provided without a deployment mechanism without departing from the present invention. Furthermore, it will be appreciated that the deployment mechanism 54 may be used with other embodiments for inserting an implant into an intervertebral disc space. In all cases, the implant 10, having been deposited in the intervertebral disc space 30, facilitates normal spinal functionality over time by maintaining a restored intervertebral disc height as well as retaining motion.

Figure 14:
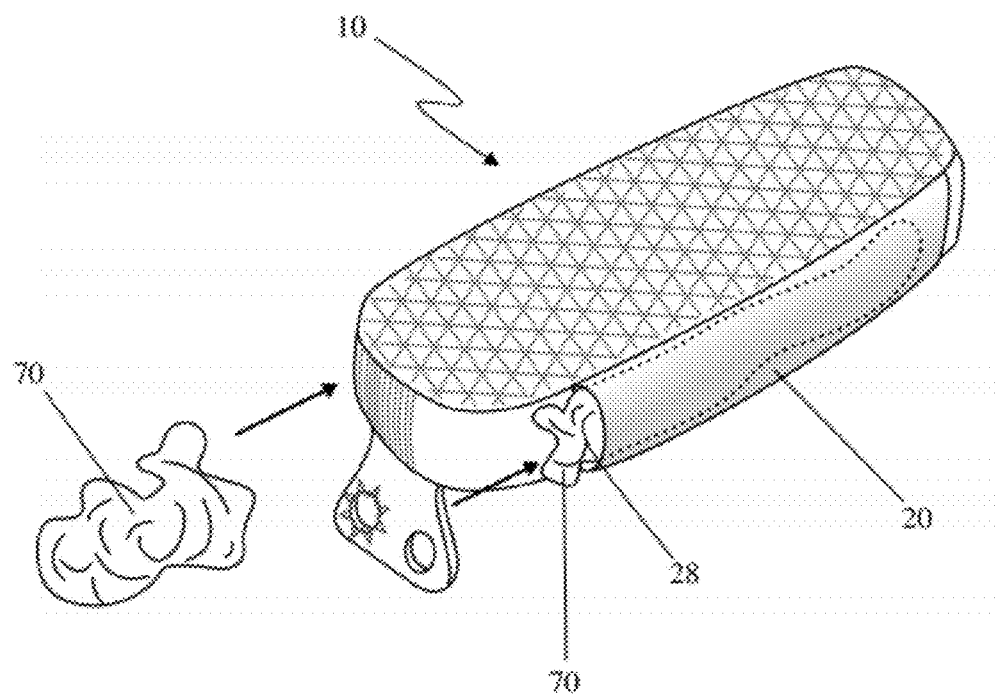
FIG. 14 is a perspective view of the implant of FIG. 3, showing the pockets of the implant being filled with textile polyester, according to one aspect of the present invention.
Figure 15:
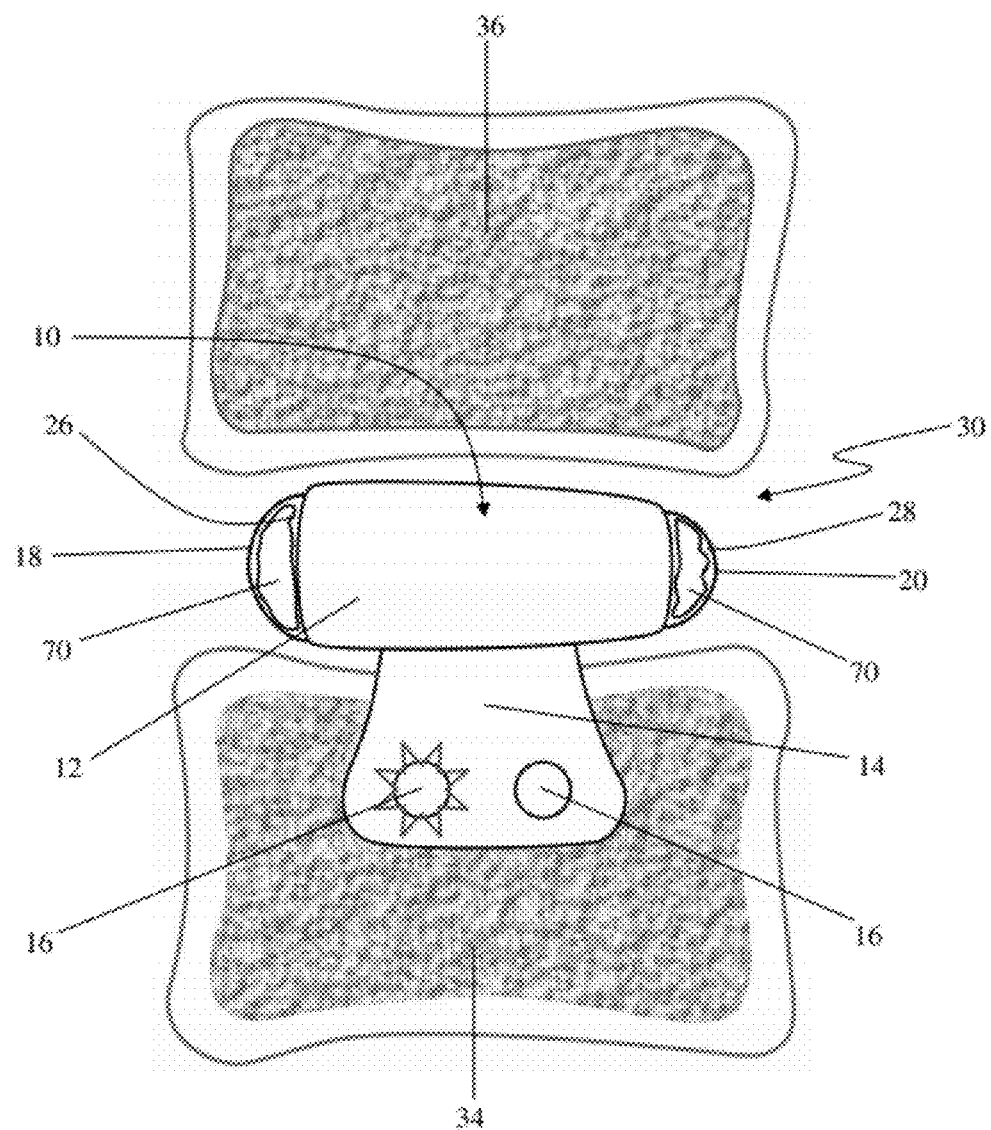
FIG. 15 is a lateral view of the implant of FIG. 14 in situ after the pockets have been filled with textile polyester.

As shown in FIGS. 14 & 15, after the implant 10 has been inserted into the intervertebral disc space 30, the pockets 18, 20 may be filled in situ, according to one embodiment of the present invention for filling an implant in situ. In this embodiment, the pockets 18, 20 of the implant 10 are filled in situ with any biocompatible material including but not limited to textile material, such as polyester 70. The polyester filling 70 enters through the openings 26, 28 of the pockets 18, 20, respectively, on the implant 10 when the implant 10 is in situ after insertion within the intervertebral disc space 30 between the vertebrae 34, 36. Filling the pockets 18, 20 in situ provides for the expansion of the physical dimensions of the implant 10.

The combination pre-filled and in situ filled implant 10 advantageously allows for minimally invasive surgical procedures. The implant 10 may be inserted through a relatively small operative corridor. Subsequently, once the implant 10 is in situ, the pockets 18, 20 may be filled with additional polyester filling 70, thereby increasing the size of the implant 10. The overall benefit is an enlarged implant 10 which may be introduced through a minimally invasive procedure, as opposed to opening an expansive operative corridor in order to accommodate a larger pre-filled implant. By filling the pockets 18, 20 of the implant 10 in situ, the final dimensions of the implant 10 may be significantly larger than as originally placed. As a result, the larger footprint of the combination pre-filled and in situ filled implant 10 provides additional support within the intervertebral disc space 30 and throughout the spine. The larger footprint of the implant 10 also allows for more tissue ingrowth due to the increased surface contact between the vertebrae 34, 36 and the implant 10, which may help to anchor the implant 10 in position.

Figure 16:
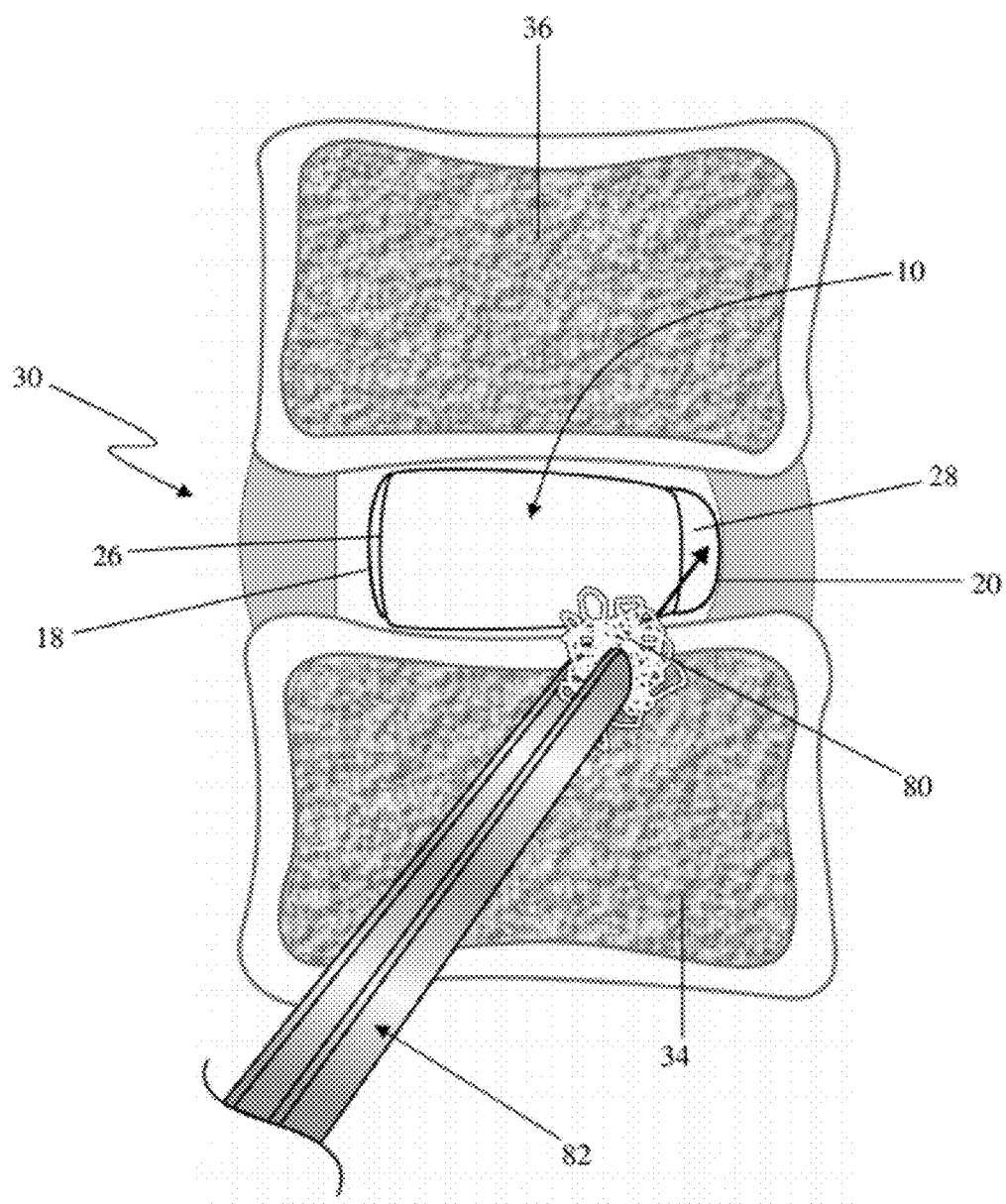
FIG. 16 is a perspective view of the implant of FIG. 3 in situ, showing the pockets being filled with fibrous polyester, according to a second aspect of the present invention.
Figure 17:
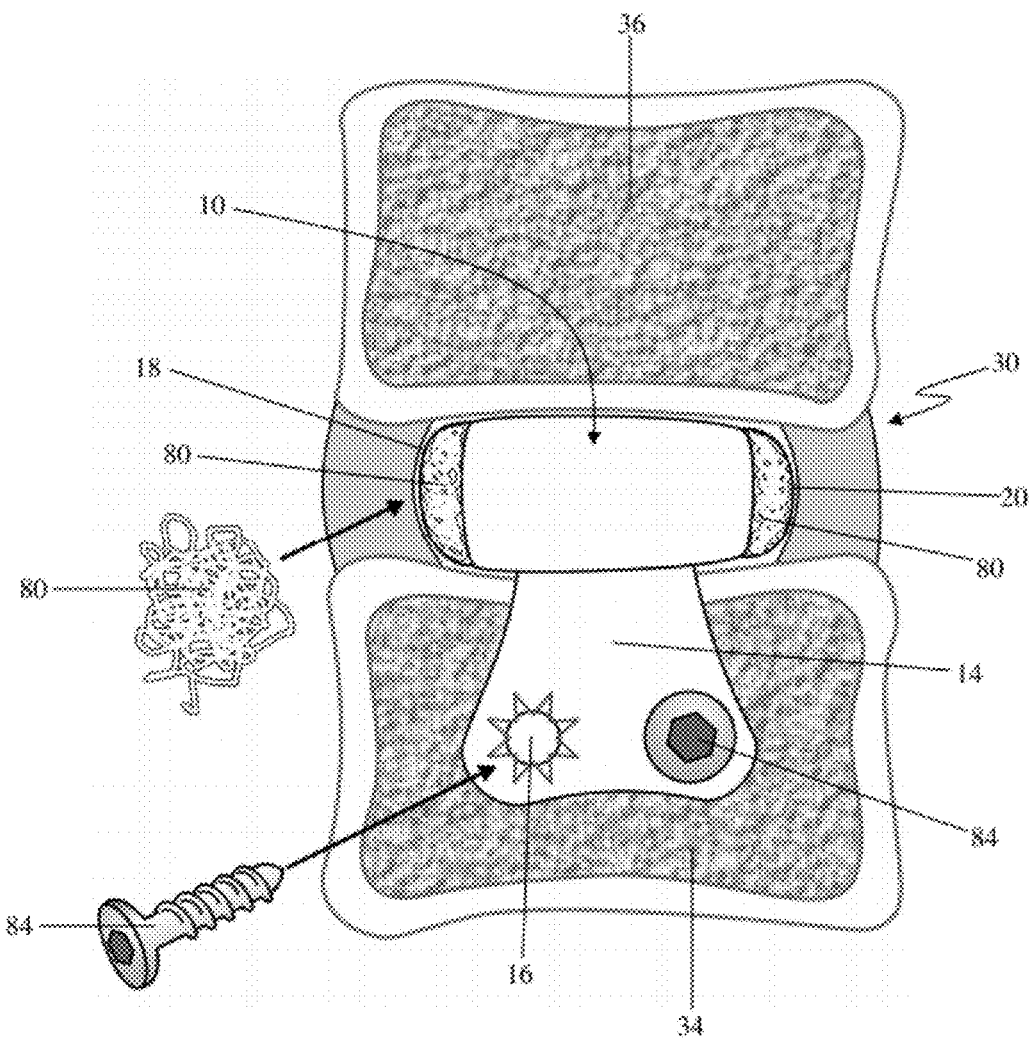
FIG. 17 is a lateral view of the implant of FIG. 16 in situ, showing the pockets of the implant being filled with fibrous polyester and the flange being secured by screws.
Figure 18:
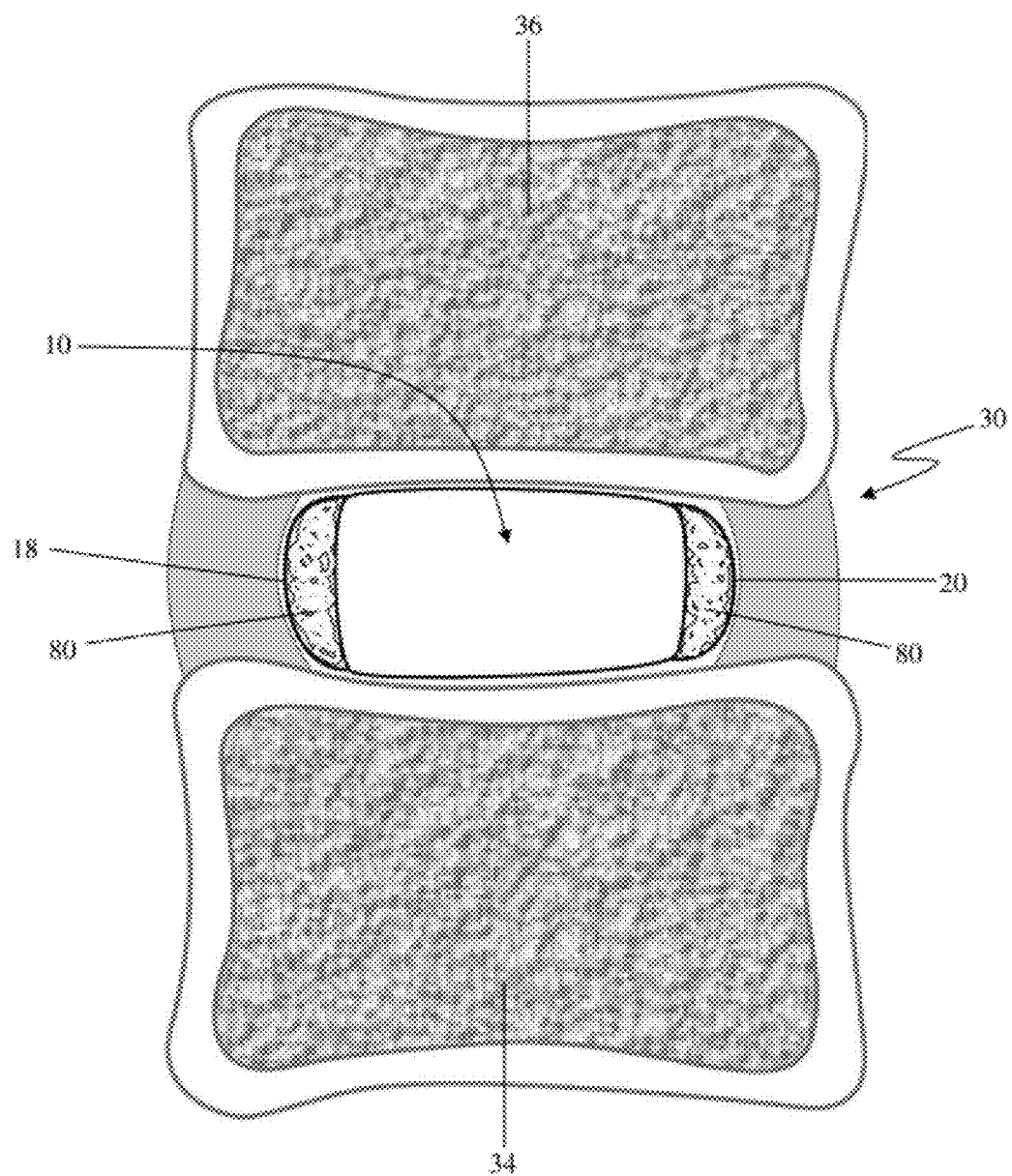
FIG. 18 is a lateral cross-sectional view of the implant of FIG. 16 in situ after the pockets have been filled with fibrous polyester.
Figure 19:
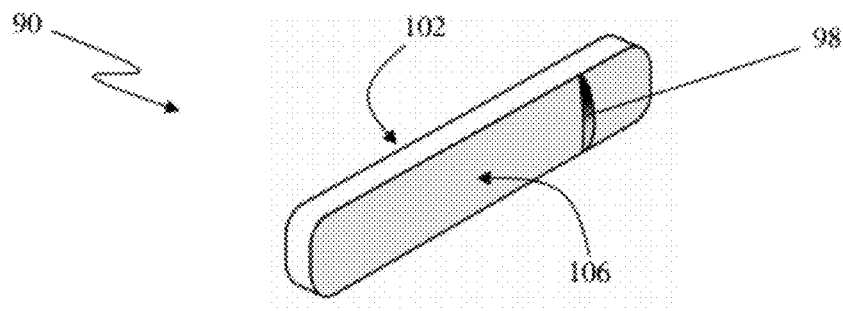
FIG. 19 is a perspective view of an embroidered polyester pad according to a third aspect of the present invention.
Figure 20:
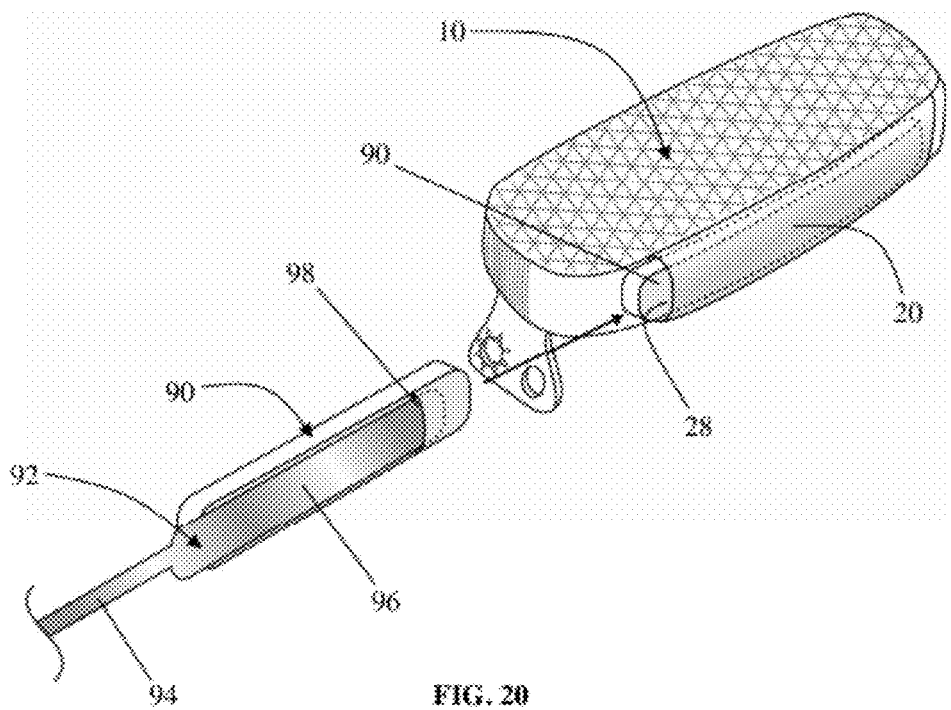
FIG. 20 is a perspective view of the implant in FIG. 3, showing the pockets being filled with the polyester pad of FIG. 19 through the use of an insertion tool.

FIGS. 16-18 illustrate one example of filling the implant 10 in situ according to another embodiment of the present invention. In this example, fibrous material 80, including but not limited to polyester, elastomeric, and/or other biocompatible fiber materials, are used to fill pockets 18, 20 of the implant 10, while the implant 10 is in situ within an intervertebral disc space 30. According to this second embodiment for filling an implant in situ, elongated forceps 82 are used to introduce the fibrous material 80 into the openings 26, 28 of the pockets 18, 20. Elongated forceps 82 may be composed of metal (e.g. titanium, stainless steel, etc.), ceramic, and/or polymer compositions. Although forceps 82 are described herein as introducing the fibrous material 80 into the pockets 18, 20 of the implant 10, it will be appreciated that any suitable means may be used to fill the pockets 18, 20 with fibrous material 80.

Once the pockets 18, 20 of the implant 10 are filled with fibrous material 80 and fully expanded, screws 84 (or any other suitable fixation elements including but not limited to anchors, nails, sutures, staples, etc.) are used to secure the implant 10 in situ. More specifically, screws 84 pass through the apertures 16 within the flange 14 of the implant 10. Screws 84 are then drilled into the adjacent inferior vertebra 34 to secure the implant 10 in position. Although implant 10 is shown as having one flange 14 with two apertures 16 and two screws 84, it will be appreciated that any number of flanges, apertures, and screws may be used to secure the implant 10 to an adjacent anatomical structure. It will also be understood that the flange 14 of the implant 10 may be affixed to the adjacent superior vertebra 36 (as opposed to the inferior vertebra 34) without departing from the scope of the present invention. In all instances, the implant 10 having been deposited within the intervertebral disc space 30 and filled in situ, provides extensive support throughout the disc space 30 thereby restoring the physiologic movements of the spine.

FIGS. 19-25 illustrate one example of a third embodiment for filling an implant 10 in situ. According to this embodiment, filler pads 90 are used to expand the side pockets 18, 20 of the implant 10 in situ after insertion of the implant 10 within the intervertebral disc space 30. Filler pads 90 may be composed of any suitable material, including but not limited to embroidered polyester, elastomeric and/or viscoelastic filing elements. Filler pads 90 are introduced into the pockets 18, 20 of the implant 10 through the use of an insertion tool 92. Insertion tool 92 has an elongated handling member 94 and a push plate 96 configured to engage with filler pads 90. Insertion tool 92 may be composed of metal (e.g. titanium, stainless steel, etc.), ceramic, and/or polymer compositions. Push plate 96 of the insertion tool 92 is generally planar rectangular in shape and vertically oriented, but may take any form necessary to interact with the filler pad 90. Filler pads 90 may have a slot 98 or pocket to accommodate the insertion tool 92.

Figure 21:
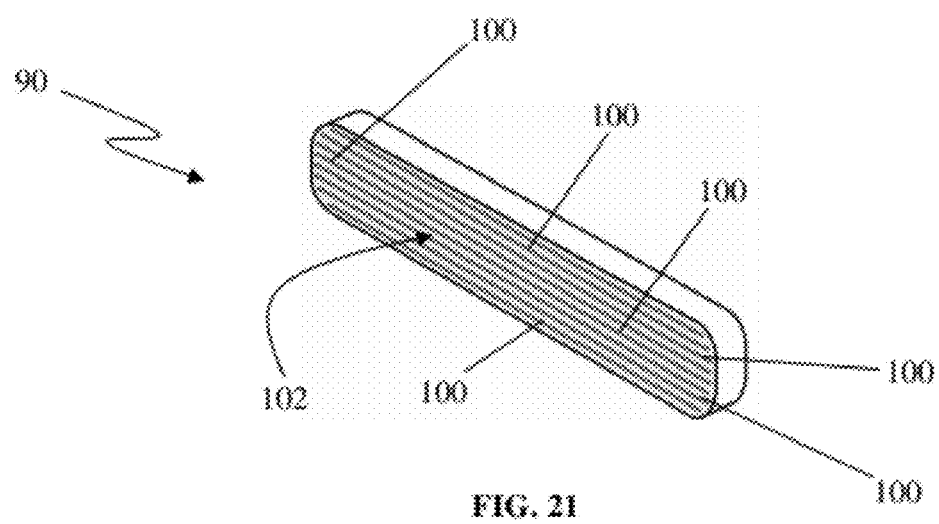
FIG. 21 is a perspective view of the medial side of the polyester pad of FIG. 19 having a longitudinally ribbed structure.
Figure 22:
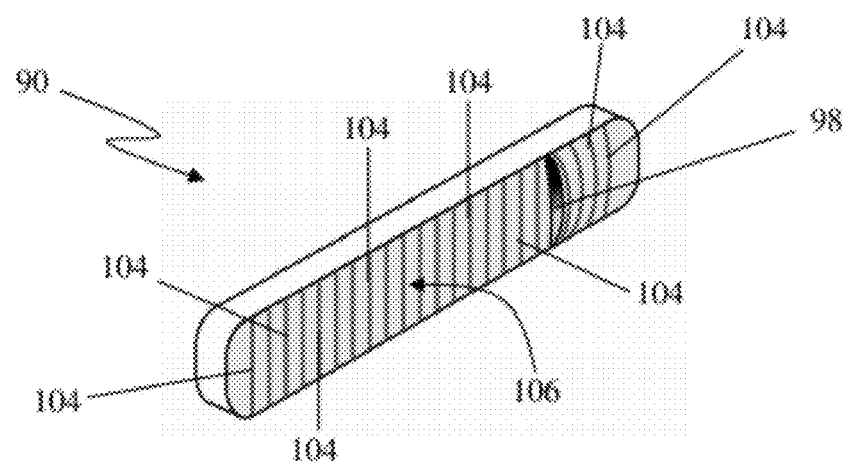
FIG. 22 is a perspective view of the lateral side of the polyester pad of FIG. 19 having a vertically ribbed structure.
Figure 23:
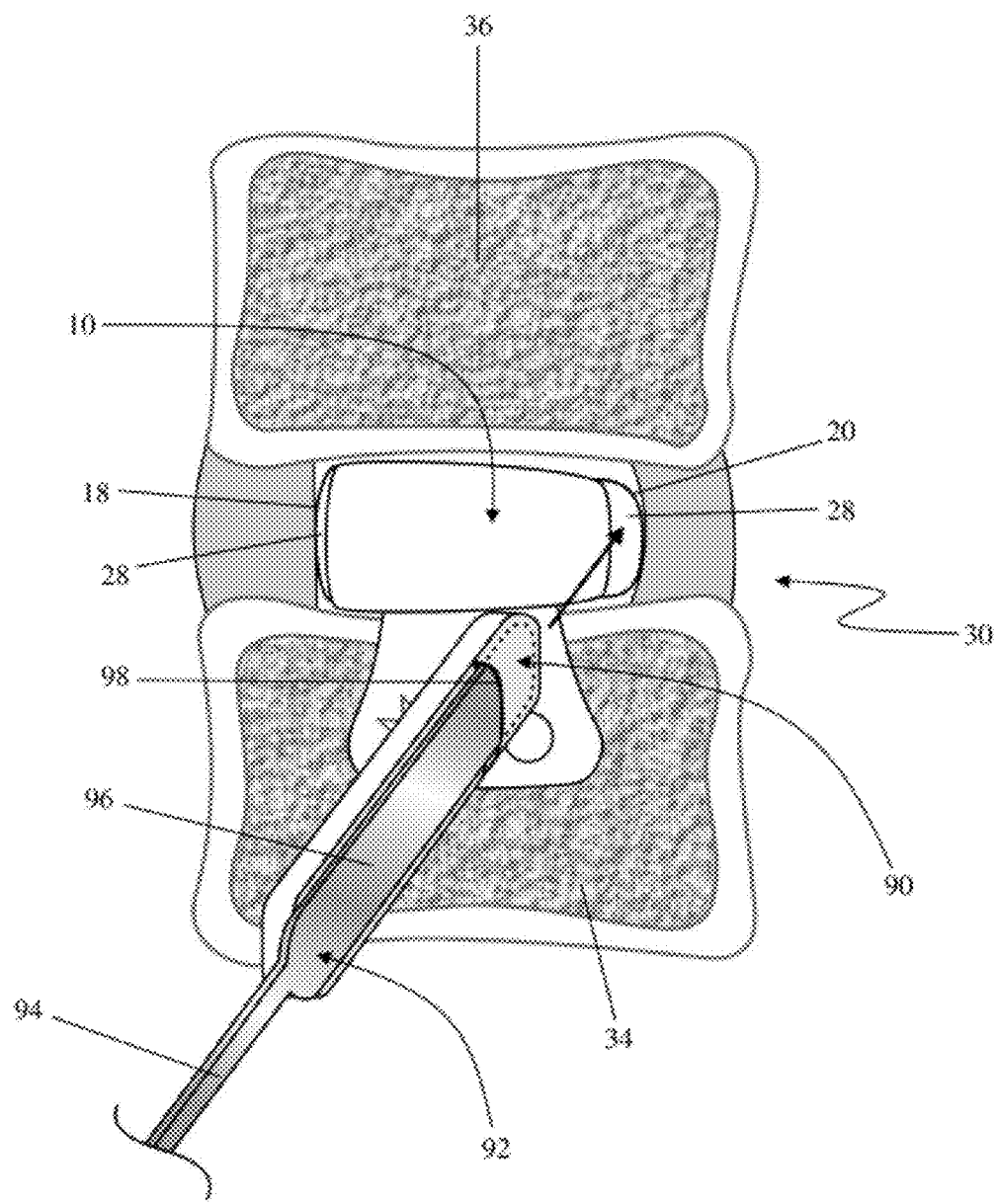
FIG. 23 is a perspective view of the implant of FIG. 3 in situ, showing the pockets being filled with the polyester pad of FIG. 19 through the use of an insertion tool.
Figure 24:
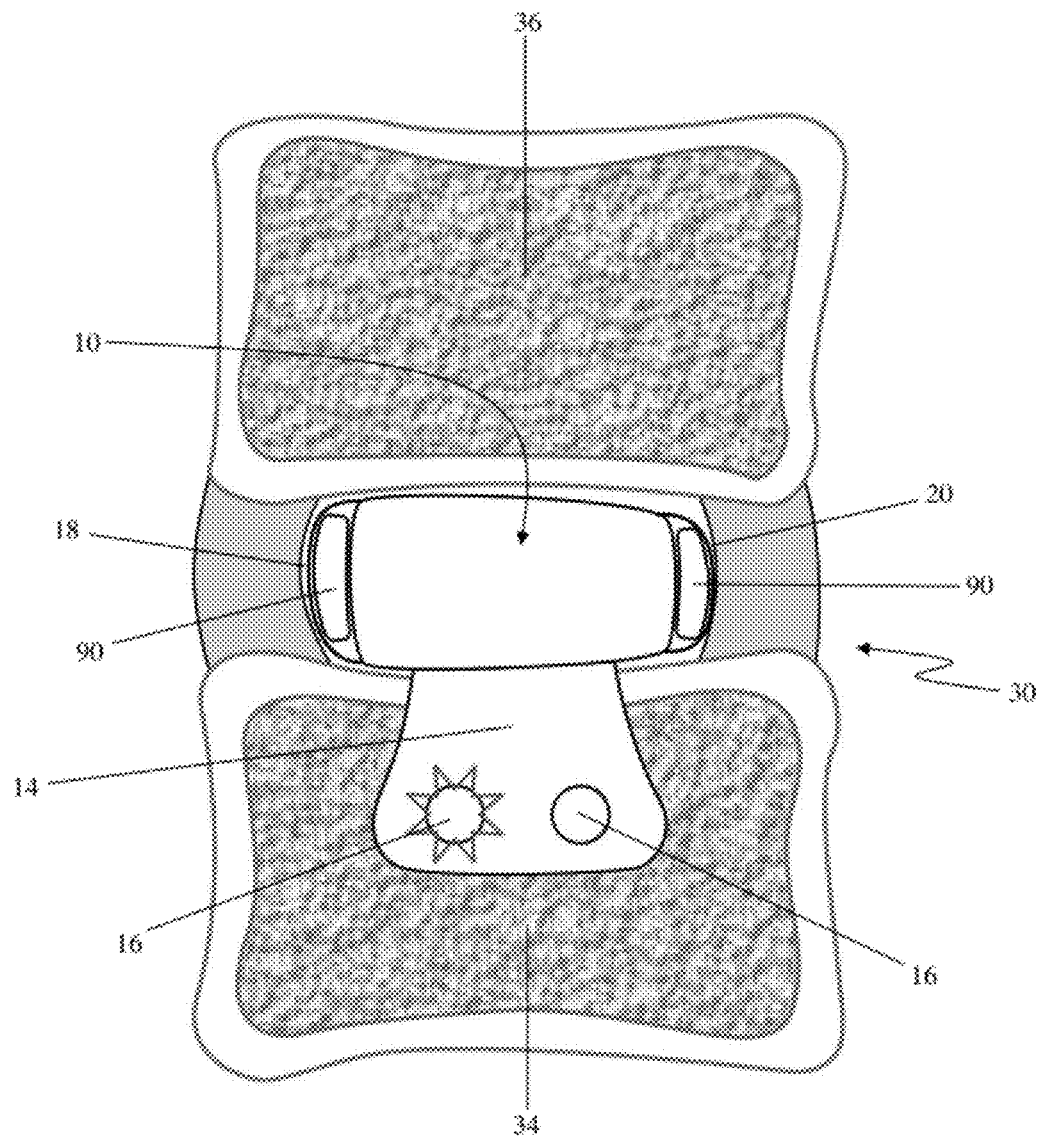
FIG. 24 is a lateral view of the implant of FIG. 23 in situ, after the pockets have been filled with polyester pads.
Figure 25:
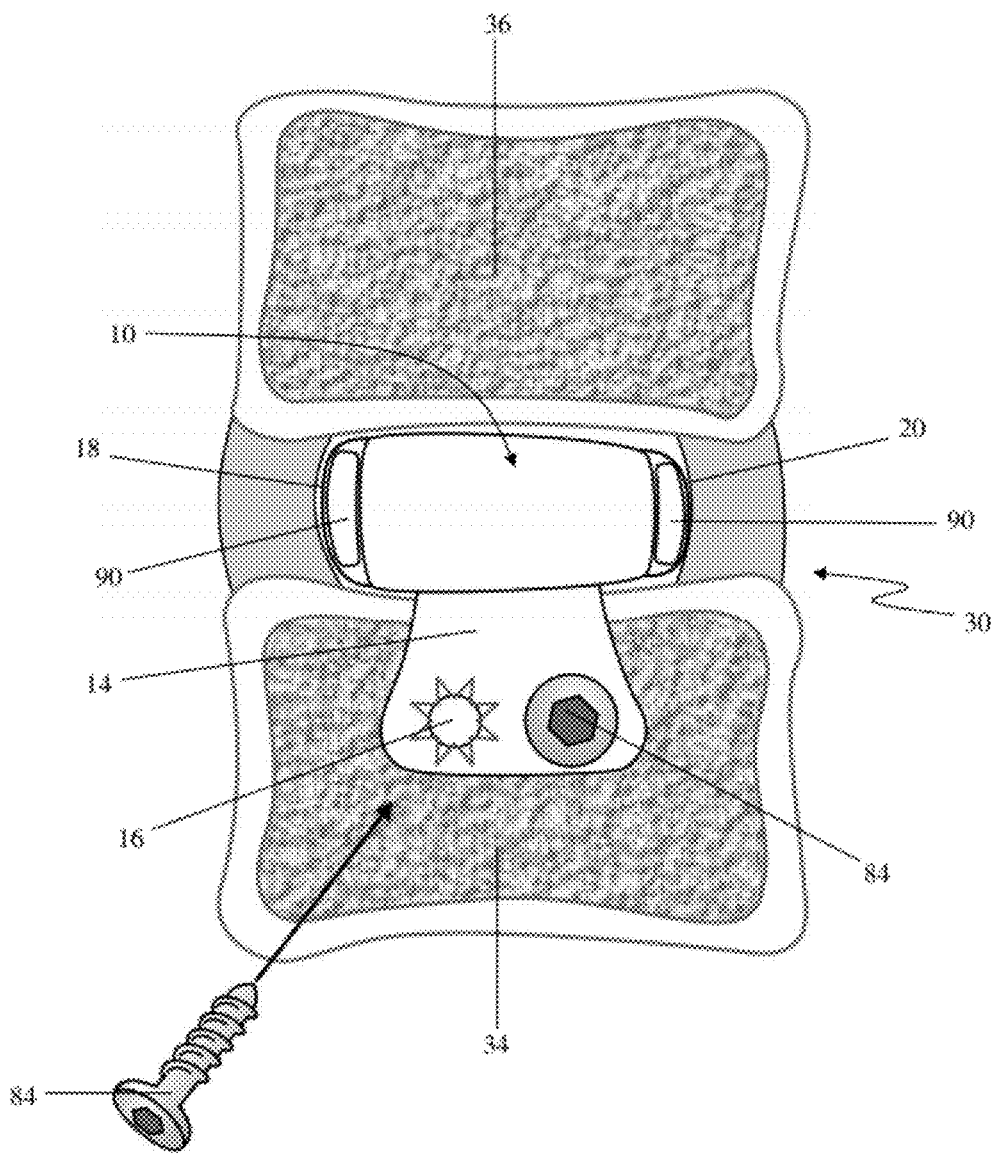
FIG. 25 is a lateral view of the implant of FIG. 24 in situ, showing the flange being secured by screws.

Filler pads 90 may be optionally provided with a longitudinally ribbed structure 100 on the medial side 102 of the filler pad 90, as shown in FIG. 21. A longitudinally ribbed structure 100 on the medial side 102 of the filler pad 90 facilitates the introduction of the filler pads 90 into the pockets 18, 20 of the implant 10 by providing longitudinal ribs 100 in the direction of insertion. Filler pads 90 may also be optionally provided with a vertically ribbed structure 104 on the lateral side 106 of the filler pad 90, as shown in FIG. 22. The vertical ribs 104 on the lateral side 106 of the filler pad 90 may engage and lock with corresponding vertical ribs (not shown) on the inside surface of the pockets 18, 20 of the implant 10. In this manner, a vertically ribbed structure 104 on the lateral side 106 of the filler pad 90 ensures that filler pads 90 are locked into place within the pockets 18, 20 of the implant 10.

Insertion tool 92 engages with the filler pad 90 by sliding the push plate 96 of the insertion tool 92 into the slot 98 of the filler pad 90. Although slideable engagement is described, any suitable means of engagement may be used to engage the insertion tool 92 with the filler pad 90, including but not limited to a threaded engagement, snapped engagement, hooks, and/or compressive force. Once the push plate 96 is inside the slot 98 of the filler pad 90, the insertion tool 92 releasably maintains the filler pad 90 in the proper orientation for insertion of the filler pad 90 into the pocket 20 of the implant 10, while the implant 10 is in situ within an intervertebral disc space 30. The filler pad 90 may then be introduced through the opening 28 of the pocket 20 of the implant 10 while engaged with the insertion tool 92 and thereafter released into the pocket 20 of the implant 10. Another filler pad 90 is similarly inserted into the other pocket 18 of the implant 10. In this way, the pockets 18, 20 of the implant 10, having been filled in situ, provide a larger footprint and additional support within the intervertebral disc space 30.

Once the pockets 18, 20 of the implant 10 are fully expanded with filler pads 90, screws 84 (or any other suitable affixation elements including but not limited to anchors, nails, sutures, staples, etc.) may be used to secure the implant 10 in situ. More specifically, screws 84 pass through the apertures 16 within the flange 14 of the implant 10. Screws 84 are then drilled into the adjacent inferior vertebra 34 to secure the implant 10 in position. Although implant 10 is shown as having one flange 14 with two apertures 16 and two screws 84, it will be appreciated that any number of flanges, apertures, and screws may be used to secure the implant 10 to an adjacent anatomical structure. It will also be understood that the flange 14 of the implant 10 may be affixed to the adjacent superior vertebra 36 (as opposed to the inferior vertebra 34) without departing from the scope of the present invention. In all instances, the implant 10 having been deposited within the intervertebral disc space 30 and filled in situ, provides extensive support throughout the disc space 30 thereby restoring the physiologic movements of the spine.

Figure 26:
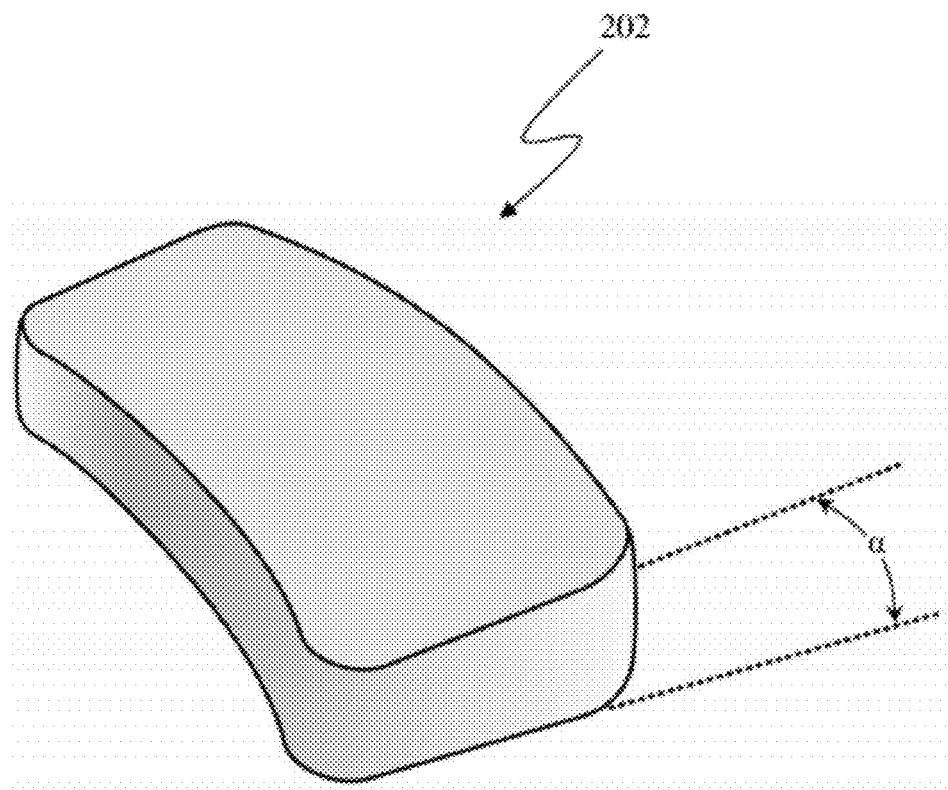
FIG. 26 is a perspective view of a postero-laterally-inserted textile-based implant having an overall curved shape and taper angle, according to one embodiment of the present invention.
Figure 27:
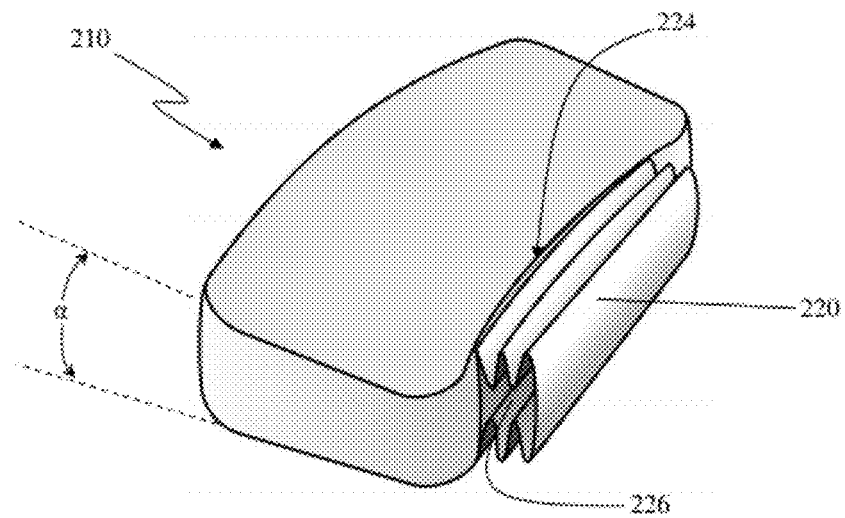
FIG. 27 is a perspective view of a postero-laterally-inserted textile-based implant having an overall curved shape, taper angle, and an expandable pocket, according to another embodiment of the present invention.
Figure 28:
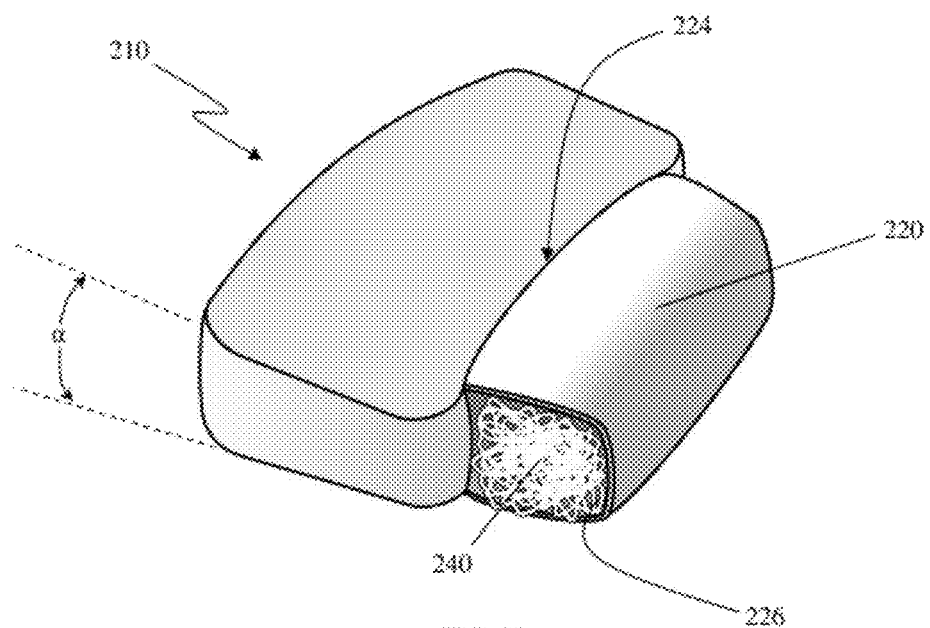
FIG. 28 is a perspective view of the implant of FIG. 27, after the pocket has been filled with fibrous polyester.
Figure 29:
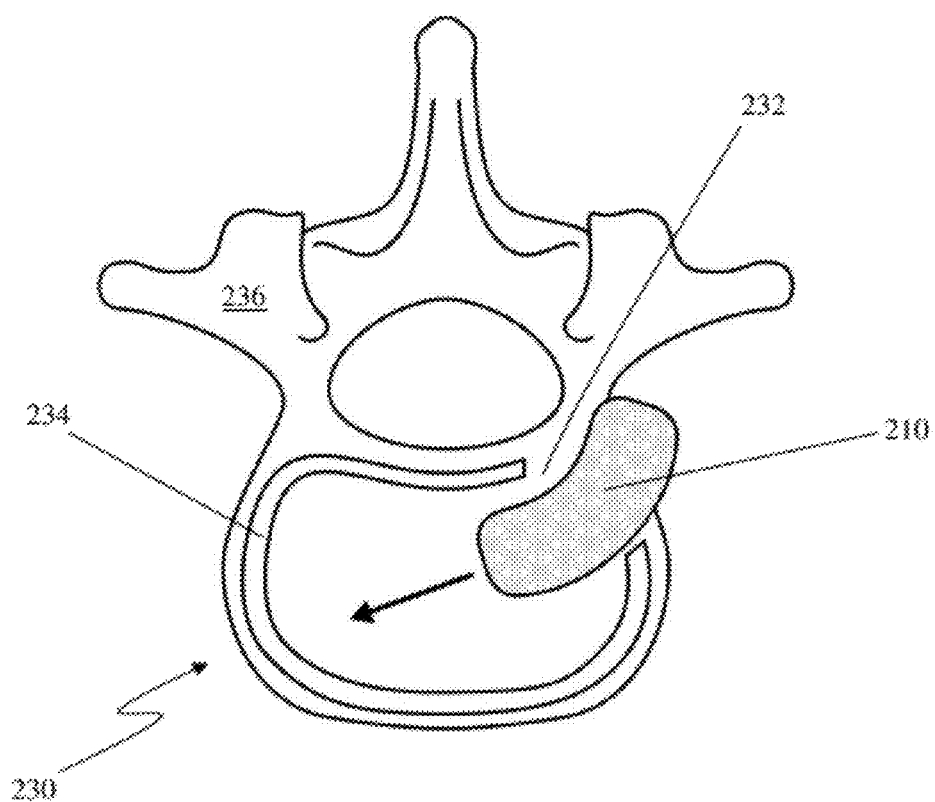
FIG. 29 is a top view of the implant of FIG. 27 being postero-laterally inserted into an intervertebral disc space.
Figure 30:
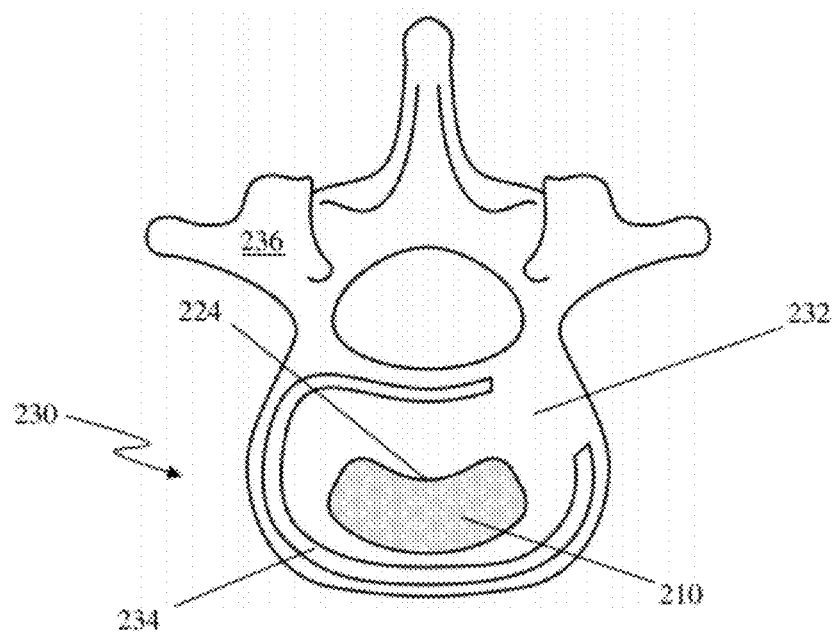
FIG. 30 is a top view of the implant of FIG. 27 in situ.
Figure 31:
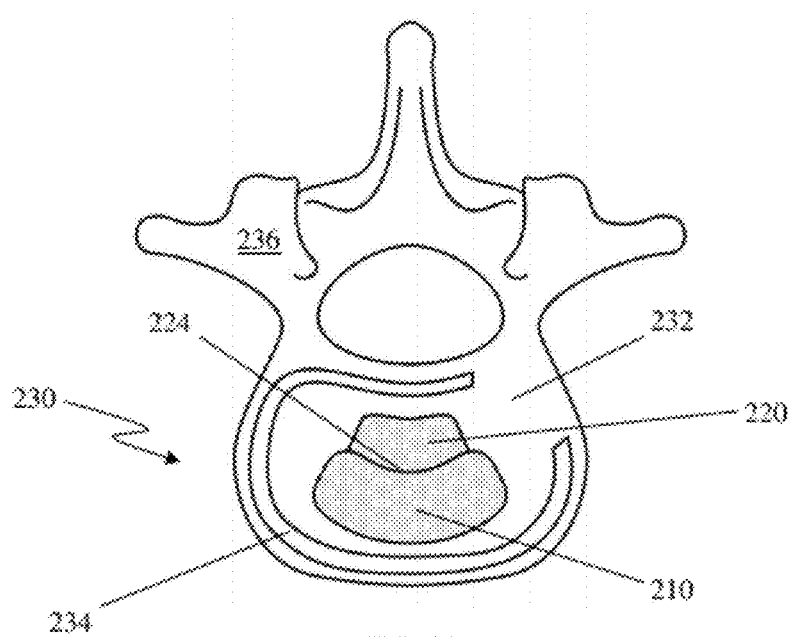
FIG. 31 is a top view of the implant of FIG. 30 in situ, after the pocket has been filled with fibrous polyester.

While a laterally-inserted combination pre-filled and in situ filled implant 10 is described above, it will be appreciated that any of the embodiments shown and described herein may be applied to a variety of spinal implants inserted through any suitable surgical technique, including but not limited to anterior, anterior-lateral, postero-lateral, and/or posterior approaches. By way of example only, FIG. 26 illustrates a pre-filled textile-based implant 202 specifically dimensioned for postero-lateral insertion, according to one embodiment of the present invention. In this embodiment, implant 202 may have an overall curved shape in order to facilitate postero-lateral insertion.

Implant 202 may also have a taper angle ($\alpha$), or a tapered cross-sectional shape, designed to match the natural lordotic and/or kyphotic angles in any given region of the spine (i.e. lordosis in the cervical and lumbar regions of the spine and kyphosis in the thoracic region of the spine). This is similar to the implant shown and described in the above-referenced '944 PCT Application. In all cases, the implant 202 restores the normal height of the intervertebral disc space, thereby advantageously preserving the natural motion of the spine.

FIGS. 27-31 illustrate a combination pre-filled and in situ filled implant 210, according to another embodiment of the present invention. Similar to the pre-filled implant 202 shown in FIG. 26, the combination pre-filled and in situ filled implant 210 has an overall curved shape in order to facilitate postero-lateral insertion, as well as a taper angle ($\alpha$) to match the natural curvature of the spine. However, in this embodiment, the implant 210 has a pocket 220 (or pockets) attached to one side (or sides) of the implant 210. By way of example only, the pocket 220 is comprised of an extra layer of embroidered fabric on the posterior side 224 of the implant 210 and has an opening 226. It will be appreciated that the placement of the pocket 220 on the implant 210 is set forth by way of example only and may be varied without departing from the scope of the present invention. In all cases, pocket 220 on the implant 210 serves to expand the dimensions of the implant 210 after insertion into the intervertebral disc space 230.

The combination pre-filled and in situ filled implant 210 with pocket 220 may be inserted postero-laterally through a relatively small operative corridor and incision 232 of the intervertebral disc 234. Subsequently, once the implant 210 is within the intervertebral disc space 230 between adjacent vertebrae 236, the pocket 220 of the implant 210 is filled in situ, thereby increasing the size of the implant 210. Fibrous material 240, including but not limited to polyester, elastomeric, and/or other biocompatible fiber materials, is inserted through the opening 226 of the pocket 220 and used to fill the pocket 220 of the implant 210. The overall benefit is an enlarged implant 210 which may be introduced through a minimally invasive procedure, as opposed to opening an expansive operative corridor in order to accommodate a larger pre-filled implant. Although fibrous material 240 is shown and described herein, it will be appreciated that any suitable material, including but not limited to textile material or filler pads, may be used to expand the pocket 220 of the implant 210 in situ, without departing from the scope of the present invention.

By filling the pocket 220 of the implant 210 in situ, the final dimensions of the implant 210 may be significantly larger than as originally placed. As a result, the larger footprint of the combination pre-filled and in situ filled implant 210 provides additional support within the intervertebral disc space 230 and throughout the spine. The larger footprint of the implant 210 also provides for more tissue ingrowth due to the increased surface contact between the vertebrae 236 and the implant 210, which may help to anchor the implant 210 in position.

Figure 32:
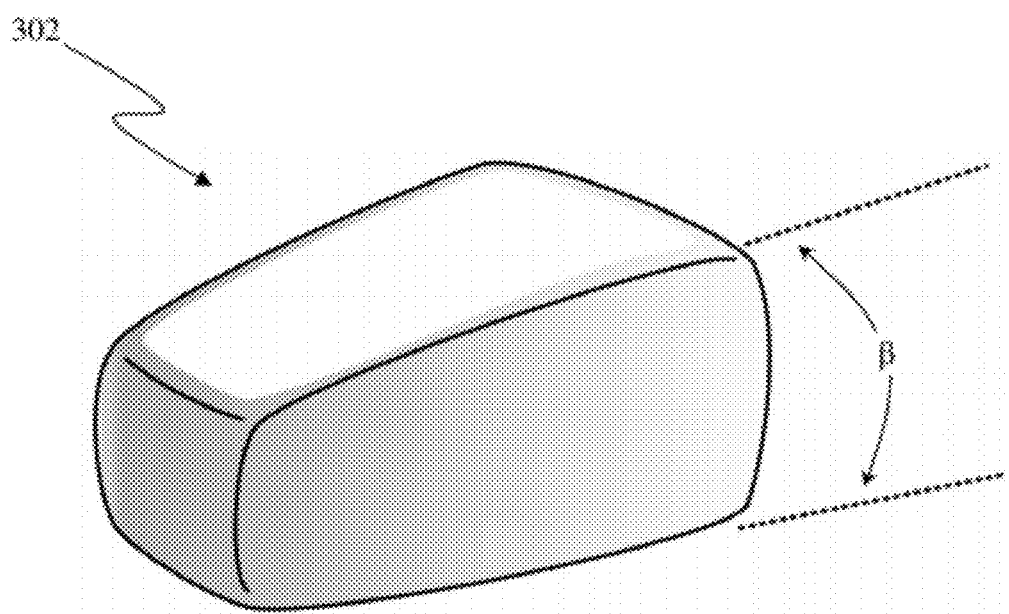
FIG. 32 is a perspective view of a posteriorly-inserted implant having an overall wedge shape and taper angle, according to one embodiment of the present invention.
Figure 33:
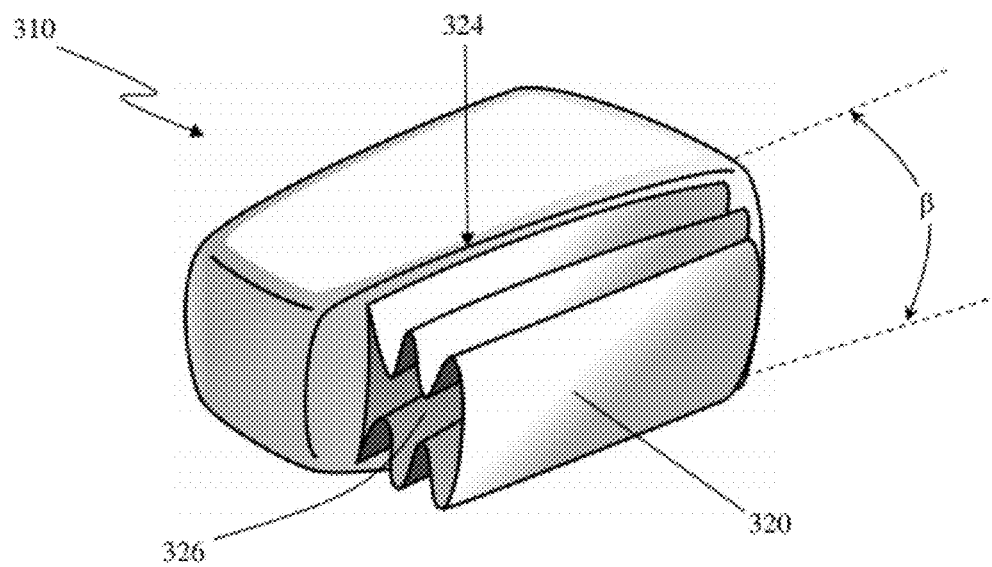
FIG. 33 is a perspective view of a posteriorly-inserted implant having an overall wedge shape, taper angle, and expandable pocket, according to another embodiment of the present invention.
Figure 34:
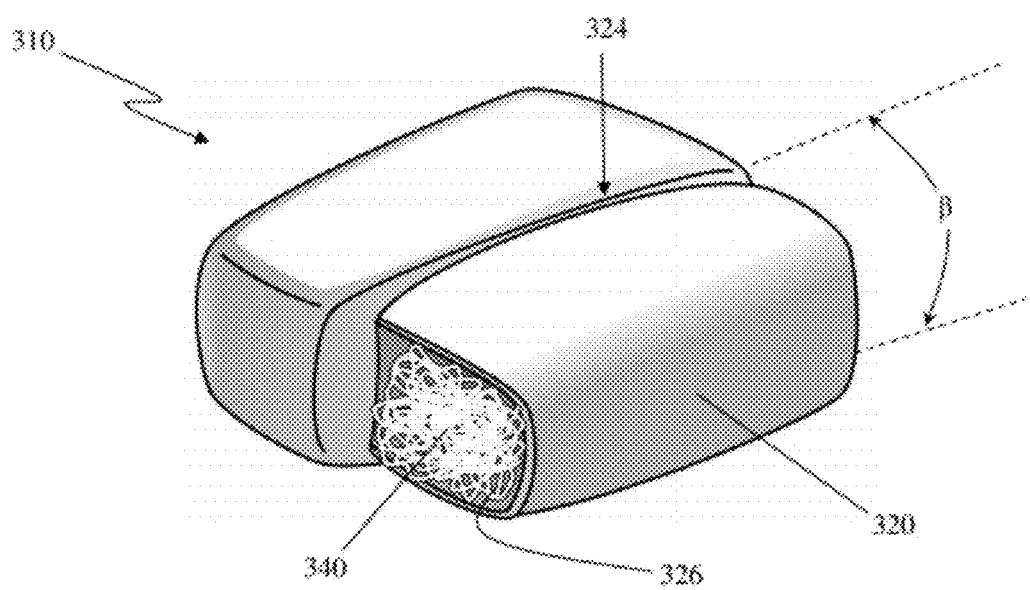
FIG. 34 is a perspective view of the implant in FIG. 33 after the pocket has been filled with fibrous polyester.

FIG. 32 illustrates an example of a pre-filled textile-based implant 302 specifically dimensioned for posterior insertion, according to one embodiment of the present invention. In this embodiment, implant 302 has an overall wedge shape in order to facilitate posterior insertion, as well as a taper angle (β) to match the natural curvature of the spine.

FIGS. 33-37 illustrate a combination pre-filled and in situ filled implant 310, according to another embodiment of the present invention. Similar to the pre-filled implant 302 shown in FIG. 32, the posteriorly-inserted combination pre-filled and in situ filled implant 310 has an overall wedge shape in order to facilitate posterior insertion, as well as a taper angle (β) to match the natural curvature of the spine. However, in this embodiment, the implant 310 has a pocket 320 (or pockets) attached to one side (or sides) of the implant 310. By way of example only, the pocket 320 is comprised of an extra layer of embroidered fabric on the medial side 324 of the implant 310 and has an opening 326. It will be appreciated that the placement of the pocket 320 on the implant 310 is set forth by way of example only, and may be varied without departing from the scope of the present invention. In all cases, pocket 320 on the implant 310 serves to expand the dimensions of the implant 310 after insertion into the intervertebral disc space 330.

By way of example only, two combination pre-filled and in situ filled implants 310 with pockets 320 may be inserted posteriorly through a relatively small operative corridor and incision 332 of the intervertebral disc 334. Subsequently, once the implants 310 are within the intervertebral disc space 330 between adjacent vertebrae 336, the pockets 320 of the implants 310 are filled in situ, thereby increasing the size of each implant 310. Fibrous material 340, including but not limited to polyester, elastomeric, and/or other biocompatible fiber materials, is inserted through the openings 326 of each pocket 320 and may be used to fill the pockets 320 of the implants 310. The overall benefit are two enlarged implants 310 which are introduced through a minimally invasive procedure, as opposed to opening an expansive operative corridor in order to accommodate a larger pre-filled implant.

Figure 35:
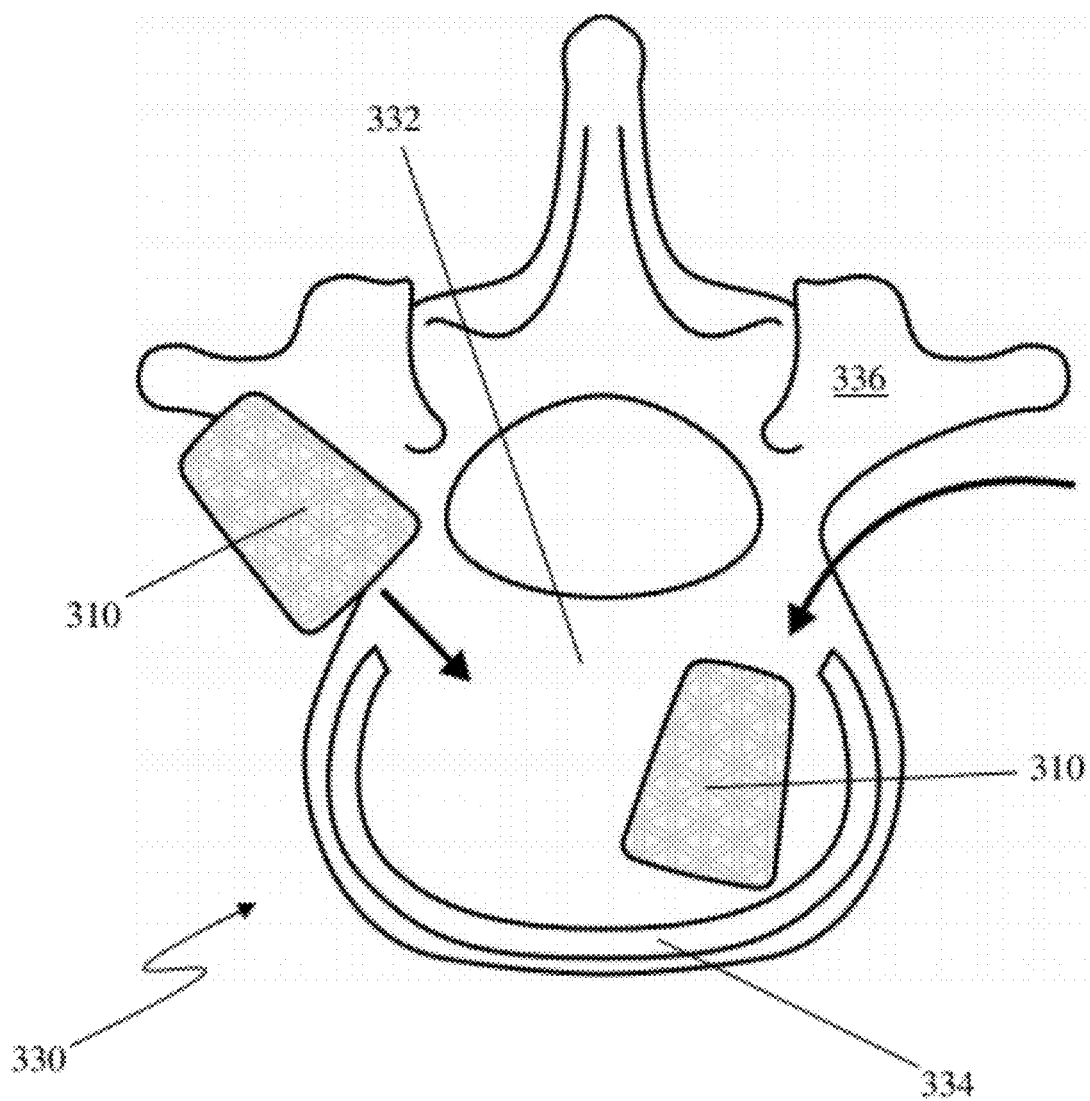
FIG. 35 is a top view of two implants of FIG. 32 being posteriorly inserted into an intervertebral disc space.
Figure 36:
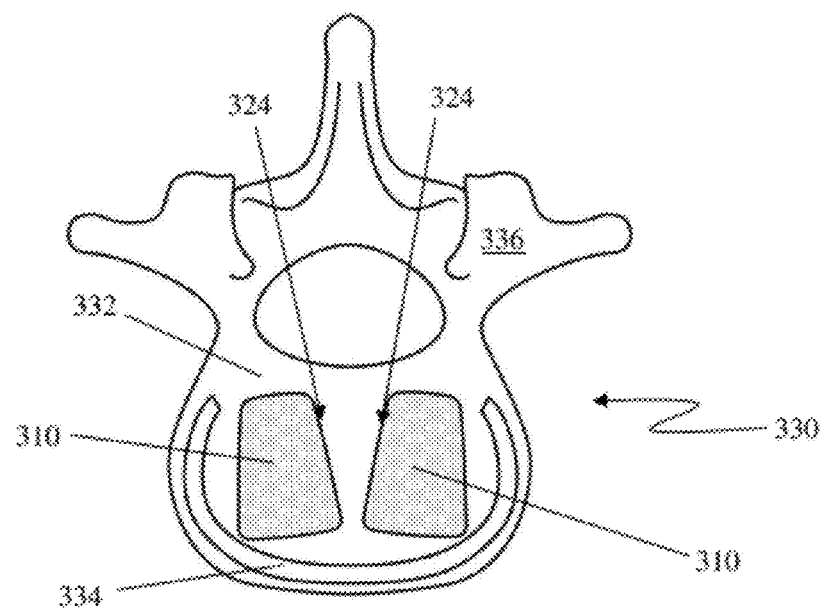
FIG. 36 is a top view of the two implants of FIG. 35 in situ.
Figure 37:
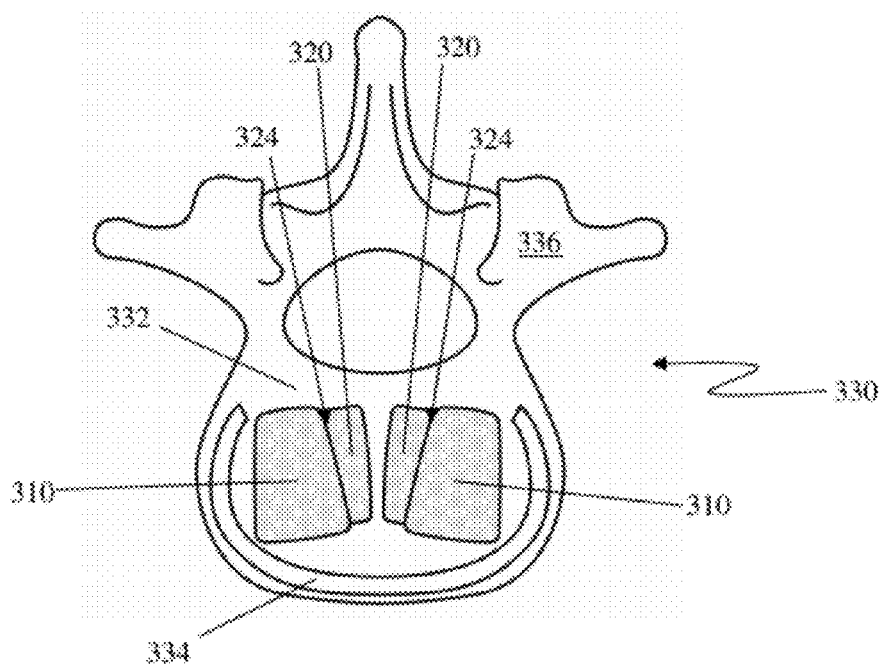
FIG. 37 is a top view of the two implants of FIG. 36 in situ, after the pockets have been filled with fibrous polyester.

Although fibrous material 340 is shown and described herein, it will be appreciated that any suitable material, including but not limited to textile material or filler pads, may be used to expand the pockets 320 of the implants 310 in situ. The number of implants (i.e. two) shown and described in FIGS. 35-37 is set forth by way of example only, and may be varied without departing from the scope of the present invention.

It is envisioned that the pocket feature of the implants 10, 210, 310 is not limited to the textile-based implants 10, 210, 310 described herein, but rather may be integrated into any surgical implant. By way of example only, a polymeric disc prosthesis (not shown) may include an outer jacket having pockets in order to facilitate the expansion of the implant's dimensions while in situ. Although not shown, instead of having pockets 18, 20, 220, 320, the combination pre-filled and in situ filled implant 10, 210, 310 may alternatively include an opening into the core of the implant 10, 210, 310 itself, in which additional filling may be introduced once the implant is in situ within the intervertebral disc space 30, 230, 330. In all cases, the implant, having been filled in situ, allows for a minimally invasive surgical technique while advantageously providing extensive support throughout the intervertebral disc space. It will also be appreciated that the implants 10, 210, 310 described herein are not limited to spinal surgery, but may be used for many different types of orthopedic applications in any part of the body.

While this invention has been described in terms of a best mode for achieving this invention's objectives, it will be appreciated by those skilled in the art that variations may be accomplished in view of these teachings without deviating from the spirit or scope of the invention.

What is claimed is:

1. A textile-based intervertebral implant comprising:
  a core encapsulated by a textile fabric jacket, said jacket including opposite first and second sides, opposite top and bottom vertebral contacting surfaces, and opposite first and second lateral sides, wherein the distance between said first and second sides defines a length, the distance between said top and bottom surfaces defines a height, and the distance between said first and second lateral sides defines a width; and
  at least one pocket attached to at least one of the opposite first and second sides, said pocket being dimensioned to receive at least one filling element and expandable from a first, pre-implantation configuration to a second, post-implantation configuration such that the pocket expands at least one-fourth the length of said jacket in said second configuration.

2. The implant of claim 1, wherein said implant has at least one of an anatomical dome shape and a tapered shape to match the natural curvature of the spine.

3. The implant of claim 1, wherein said implant is generally rectangular in shape.

4. The implant of claim 1, wherein said core comprises at least one textile, metal, and polymeric material.

5. The implant of claim 1, wherein said at least one pocket is attached to a posterior side of said implant.

6. The implant of claim 1, wherein said at least one pocket comprises an opening to insert a filling element into said at least one pocket.

7. The implant of claim 1, wherein said at least one pocket comprises an extra layer of embroidered fabric attached to at least one of said first side and said second side of said implant.

8. The implant of claim 1, wherein said at least one pocket comprises an integrally formed embroidered fabric within the jacket.

9. The implant of claim 1, wherein said jacket is formed from at least one fibrous material from the group consisting of polyester fiber, polypropylene, polyethylene, ultra high molecular weight polyethylene, poly-ether-ether-ketone, carbon fiber, glass, glass fiber, polyaramide, metal, copolymers, polyglycolic acid, polylactic acid, polylactic acid, biodegradable fibers, nylon, silk, cellulosic and polycaprolactone fibers.

10. The method of claim 1, wherein said jacket comprises a structure formed by at least one of embroidery, weaving, three-dimensional waving, knitting, three-dimensional knitting, injection molding, compression molding, cutting woven fabrics and cutting knitted fabrics.

11. The implant of claim 1, wherein said implant has an overall curved shape.

12. The implant of claim 1, wherein said at least one pocket is attached to an anterior side of said implant.

* * * * *